US012716889B2

(12) United States Patent
Chua et al.

(10) Patent No.: US 12,716,889 B2
(45) Date of Patent: Aug. 25, 2026

(54) MICROFLUIDIC-BASED DEVICE FOR IN VIVO WOUND INFECTION MODEL AND USES THEREOF

(71) Applicants: The Hong Kong Polytechnic University, Hong Kong (CN); City University of Hong Kong, Hong Kong (CN)

(72) Inventors: Song Lin Chua, Hong Kong (CN); Bee Luan Khoo, Hong Kong (CN); Yang Liu, Hong Kong (CN)

(73) Assignees: The Hong Kong Polytechnic University, Hong Kong (CN); City Unversity of Hong Kong, Hong Kong (CN)

(*) Notice: Subject to any disclaimer, the term of this patent is extended or adjusted under 35 U.S.C. 154(b) by 421 days.

(21) Appl. No.: 18/555,292

(22) PCT Filed: Apr. 22, 2022

(86) PCT No.: PCT/CN2022/088369
§ 371 (c)(1),
(2) Date: Oct. 13, 2023

(87) PCT Pub. No.: WO2022/228288
PCT Pub. Date: Nov. 3, 2022

(65) Prior Publication Data

US 2024/0192199 A1 Jun. 13, 2024

Related U.S. Application Data

(60) Provisional application No. 63/201,348, filed on Apr. 26, 2021.

(51) Int. Cl.
*G01N 33/50* (2006.01)
*B01L 3/00* (2006.01)

(52) U.S. Cl.
CPC .... *G01N 33/5088* (2013.01); *B01L 3/502761* (2013.01); *G01N 33/5023* (2013.01);
(Continued)

(58) Field of Classification Search
CPC ........... G01N 33/5088; G01N 33/5091; G01N 2333/4603; B01L 3/502761;
(Continued)

(56) References Cited

U.S. PATENT DOCUMENTS 6,193,647 B1 * 2/2001 Beebe .................... A61D 19/04 600/33
6,656,449 B1 * 12/2003 Serbedzija ......... A61K 49/0021 424/9.34

(Continued)

OTHER PUBLICATIONS

Yang, F., Gao, C., Wang, P., Zhang, G.-J. & Chen, Z. Fish-on-a-chip: microfluidics for zebrafish research. Lab on a Chip 16, 1106-1125, doi:10.1039/C6LC00044D (2016).

(Continued)

*Primary Examiner* — Jonathan M Hurst
(74) *Attorney, Agent, or Firm* — S&F/WEHRW

(57) ABSTRACT

The present invention provides an integrated microfluidic-based device for establishing a wound infection in vivo model suitable for high throughput bioassay such as potential drug screening, in vivo dosing optimization, host-microbe or microbe-microbe interactions under the influence of specific agents of interest, and studying regulatory mechanisms of certain inflammatory diseases relating to or arising from the wound infection. The present invention allows direct qualitative and quantitative assessments of specific markers expressed due to the wound infection by one or more microbes devoid of cell sorting, isolation, or labelling as in other conventional in vivo models or methods.

30 Claims, 12 Drawing Sheets

(52) U.S. Cl.
CPC ... *B01L 2200/0647* (2013.01); *B01L 2200/10* (2013.01); *B01L 2200/16* (2013.01); *B01L 2300/087* (2013.01); *B01L 2300/0874* (2013.01); *G01N 2333/21* (2013.01); *G01N 2333/245* (2013.01); *G01N 2333/4603* (2013.01); *G01N 2500/10* (2013.01)

(58) Field of Classification Search
CPC ....... B01L 2200/0647; B01L 2300/087; B01L 2300/0883
See application file for complete search history.

(56) References Cited

U.S. PATENT DOCUMENTS

| | | | | |
|---|---|---|---|---|
| 11,959,057 | B2 * | 4/2024 | Voronov | C12M 25/02 |
| 2004/0143865 | A1 * | 7/2004 | Rubinstein | G01N 33/5088<br>800/3 |
| 2013/0096029 | A1 * | 4/2013 | Sia | C12M 23/16<br>506/10 |
| 2013/0190212 | A1 * | 7/2013 | Handique | G01N 1/20<br>506/40 |
| 2015/0343444 | A1 * | 12/2015 | Manalis | B01L 3/502761<br>435/309.1 |
| 2017/0312748 | A1 * | 11/2017 | Cornaglia | B01L 3/5085 |
| 2019/0009274 | A1 * | 1/2019 | Novak | G01N 33/5088 |

OTHER PUBLICATIONS

Saraceni, P. R., Romero, A., Figueras, A. & Novoa, B. Establishment of Infection Models in Zebrafish Larvae (Danio rerio) to Study the Pathogenesis of Aeromonas hydrophila. Frontiers in Microbiology7, doi: 10.3389/fmicb.2016.01219 (2016).

Clatworthy, A. E. et al. < em>Pseudomonas aeruginosa</em> Infection of Zebrafish Involves both Host and Pathogen Determinants. 77, 1293-1303, doi:10.1128/IAI.01181-08 %J Infection and Immunity (2009).

Rauta, P. R., Nayak, B. & Das, S. Immune system and immune responses in fish and their role in comparative immunity study: a model for higher organisms. Immunol Lett 148, 23-33, doi: 10.1016/j.imlet.2012.08.003 (2012).

Khalili, A. & Rezai, P. Microfluidic devices for embryonic and larval zebrafish studies. Brief Funct Genomics 18, 419-432, doi:10.1093/bfgp/elz006 (2019).

Holloway, B. W. & Morgan, A. F. Genome Organization in Pseudomonas. Annual Review of Microbiology 40, 79-105, doi:10.1146/annurev.mi.40.100186.000455 (1986).

Rybtke, M. T. et al. Fluorescence-based reporter for gauging cyclic di-GMP levels in Pseudomonas aeruginosa. Appl Environ Microbiol 78, 5060-5069, doi: 10.1128/AEM.00414-12 (2012).

Liu, S. Y., Leung, M. M.-L., Fang, J. K.-H. & Chua, S. L. Engineering a microbial 'trap and release' mechanism for microplastics removal. Chemical Engineering Journal 404, 127079, doi:https://doi.org/10.1016/j.cej.2020.127079 (2021).

Visca, P., Ciervo, A. & Orsi, N. Cloning and nucleotide sequence of the pvdA gene encoding the pyoverdin biosynthetic enzyme L-ornithine N5-oxygenase in Pseudomonas aeruginosa. Journal of Bacteriology176, 1128, doi: 10.1128/jb.176.4.1128-1140.1994 (1994).

Lambertsen, L., Sternberg, C. & Molin, S. Mini-Tn7 transposons for site-specific tagging of bacteria with fluorescent proteins. Environmental Microbiology 6, 726-732, doi: 10.1111/j. 1462-2920.2004.00605.x (2004).

Chua, S. L. et al. Bis-(3'-5')-cyclic dimeric GMP regulates antimicrobial peptide resistance in Pseudomonas aeruginosa. Antimicrobial agents and chemotherapy 57, 2066-2075, doi:10.1128/AAC.02499-12 (2013).

Chen, Y. et al. Multiple diguanylate cyclase-coordinated regulation of pyoverdine synthesis in Pseudomonas aeruginosa. Environmental microbiology reports 7, 498-507, doi: 10.1111/1758-2229.12278 (2015).

Olucha, J., Meneely, K. M., Chilton, A. S. & Lamb, A. L. Two structures of an N-hydroxylating flavoprotein monooxygenase: ornithine hydroxylase from Pseudomonas aeruginosa. J Biol Chem 286, 31789-31798, doi: 10.1074/jbc. M111.265876 (2011).

Kessler, B., de Lorenzo, V. & Timmis, K. N. A general system to integrate lacZ fusions into the chromosomes of gram-negative eubacteria: regulation of the Pm promoter of the TOL plasmid studied with all controlling elements in monocopy. Molecular & general genetics : MGG 233, 293-301, doi: 10.1007/bf00587591 (1992).

Barnes, R. J., Leung, K. T., Schraft, H. & Ulanova, M. Chromosomal gfp labelling of Pseudomonas aeruginosa using a mini-Tn7 transposon: application for studies of bacteria-host interactions. Canadian journal of microbiology 54, 48-57, doi:10.1139/w07-118 (2008).

Chua, S. L. et al. Dispersed cells represent a distinct stage in the transition from bacterial biofilm to planktonic lifestyles. Nature communications 5, 4462, doi: 10.1038/ncomms5462 (2014).

* cited by examiner

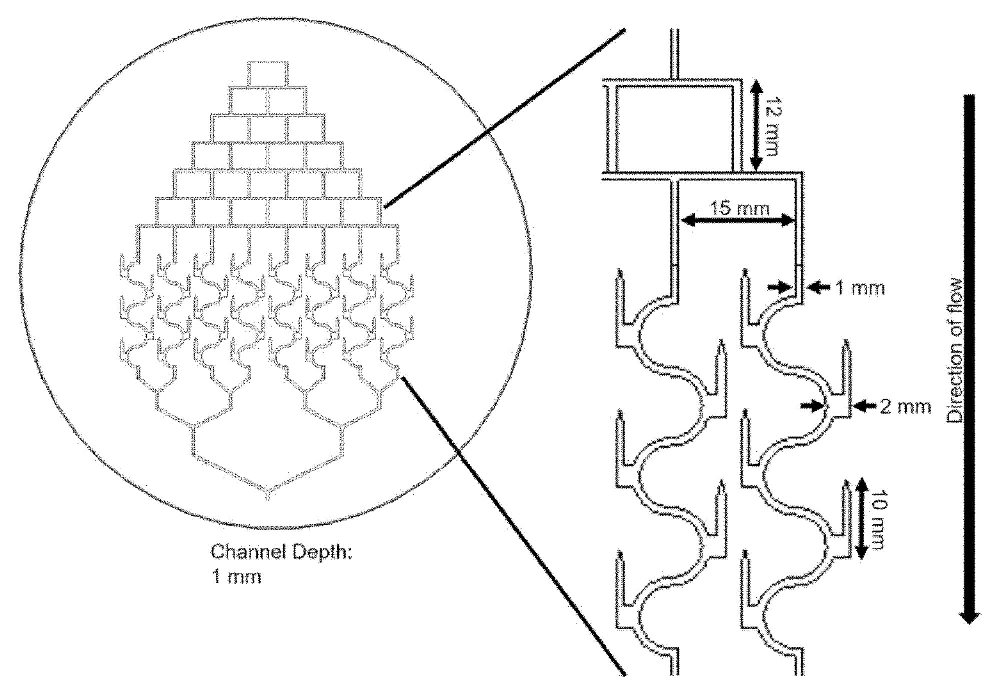
FIG. 1A
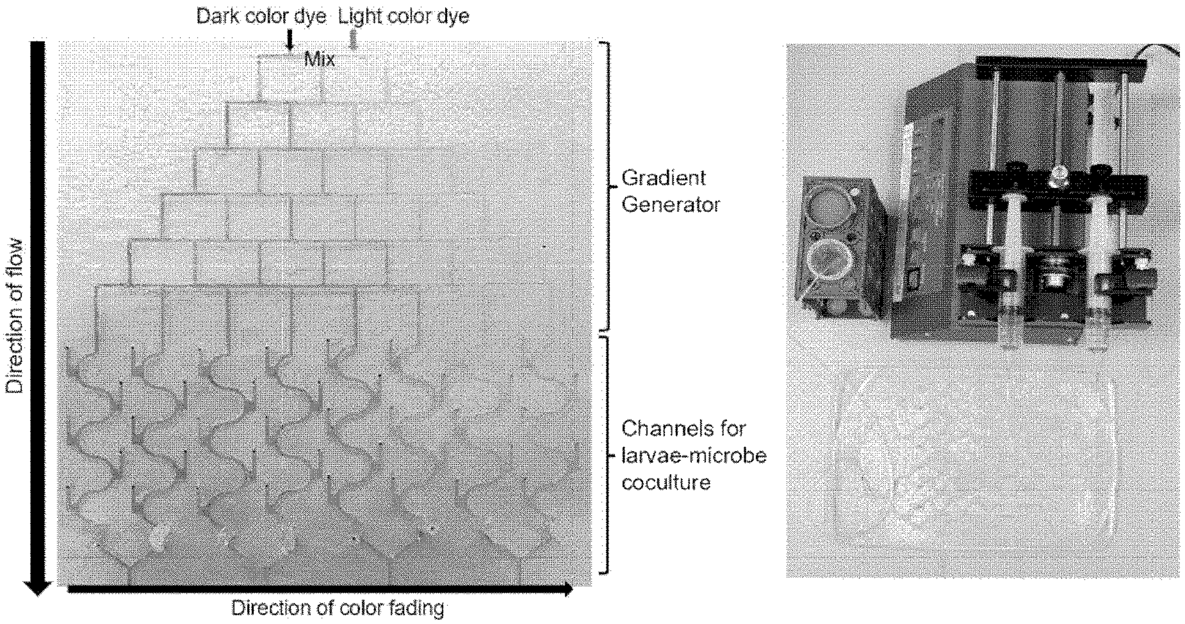
FIG. 1B
FIG. 1C

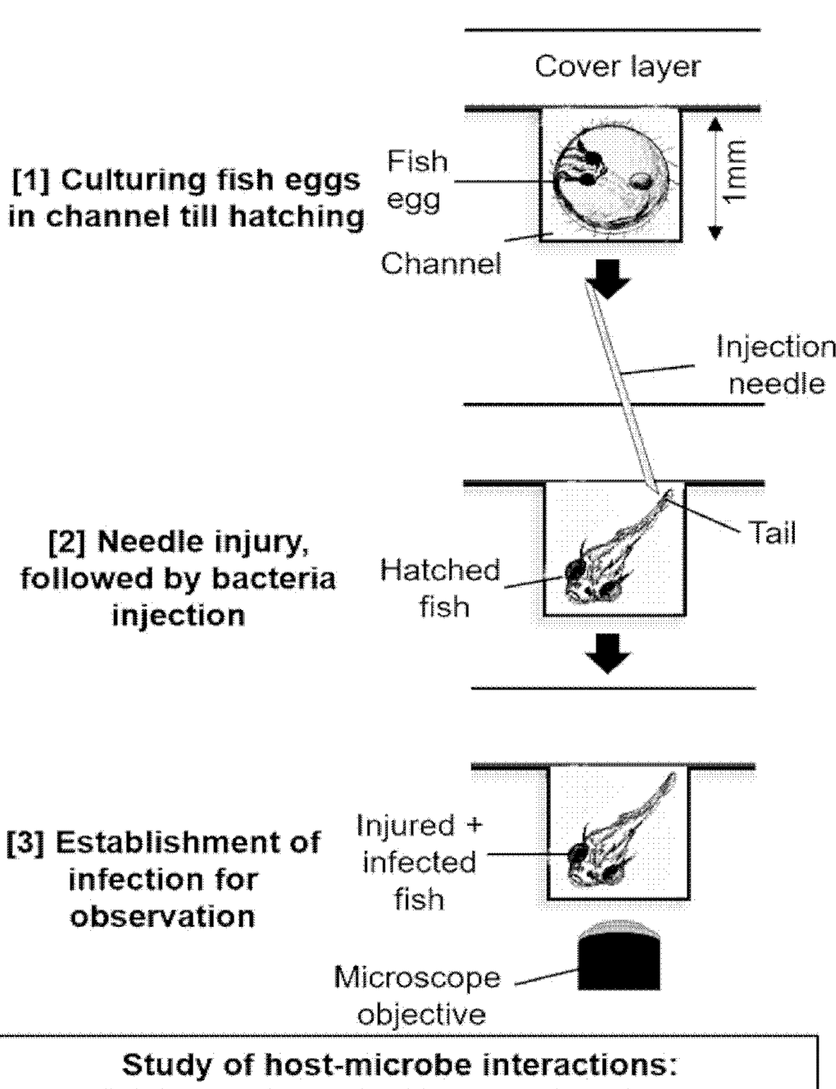

Study of host-microbe interactions:
[1] Comparison of wild-type with mutants
[2] Observation and data collection relevant to microbes and fish

Evaluation of novel antimicrobials:
[1] *In vivo* drug treatment using gradient concentrator
[2] Evaluation of microbial infection
[3] Evaluation of fish recovery

Routine screening of antibiotic efficacy in clinical isolates:
[1] Collection of clinical isolates from patients [2] *In vivo* drug treatment using gradient concentrator
[3] Evaluation of microbial infection and fish recovery

FIG. 2A

| SNP (µM) | 11 | 11 | 10.88 | 10 | 6.6 | 2.2 | 0.88 | 0 |
|---|---|---|---|---|---|---|---|---|
| Ciprofloxacin (µg/ml) | 0 | 0.34 | 0.85 | 2.56 | 3.825 | 4.165 | 4.25 | 4.25 |

| SNP (µM) | 11 | 11 | 10.88 | 10 | 6.6 | 2.2 | 0.88 | 0 |
|---|---|---|---|---|---|---|---|---|
| Ciprofloxacin (µg/ml) | 0 | 0.34 | 0.85 | 2.56 | 3.825 | 4.165 | 4.25 | 4.25 |

MICROFLUIDIC-BASED DEVICE FOR IN VIVO WOUND INFECTION MODEL AND USES THEREOF

CROSS-REFERENCE TO RELATED APPLICATIONS

This is a 371 application of an International Patent Application number PCT/CN2022/088369 filed Apr. 22, 2022 which claims priority from a U.S. provisional patent application No. 63/201,348 filed Apr. 26, 2021, which disclosure is incorporated herein by reference.

TECHNICAL FIELD

The present invention relates to an in vivo wound infection model established on a microfluidic-based device to provide a one-stop platform for the growth of a host, wound induction, pathogenic infection, and assays of pathogenic infections at the induced wound of the host.

BACKGROUND

Microfluidics/lab-on-the-chip devices have been used on zebrafish embryos and larvae to study organogenesis and delivery of foreign material (such as nucleic acids, proteins, nanoparticles, and dyes) for transgenics, in vitro fertilization, and drug development (Yang et al., 2016).

However, the benefits of microfluidics, such as small sample size and high-throughput screening capabilities, have not been translated into any fish-microbe (pathogenic, non-pathogenic, and commensal) study. Few studies have researched microbial interactions with fish, and they were also conducted in conventional fish tanks or Petri dishes (Saraceni et al., 2016). Fish are simple jawed vertebrates with a fundamental immune system similar to that of non-human mammals or humans, including lymphocytes, antibodies, and major histocompatibility complexes (Clatworthy et al., 2009; Rauta et al., 2012). Due to its low breeding cost, small size, and transparency, fish could also be suitably employed in microfluidic devices (Khalili & Rezai, 2019). Therefore, fish appears to be the most suitable choice among other available vertebrates for developing vertebrate-microbe interaction models.

However, no microfluidics-based vertebrate host-microbe interaction platform is available to date. Thus, there is a need to develop an integrated platform for the growth of a host, inducing wound and pathogenic infection on the host, and performing assays of the infections for point-of-care diagnosis.

SUMMARY OF THE INVENTION

Therefore, one of the main objectives of the present invention is to provide a host-microbe platform using fish as an in vivo model organism to serve as a pre-clinical animal model for high throughput screening of antimicrobials and rapid antimicrobial efficacy testing. The platform can also be applied for personalized medicine, where clinical samples could be evaluated for their virulence potential and sensitivity to antibiotics, thus improving their antimicrobial treatment.

Accordingly, the first aspect of the present invention provides a microfluidic-based device for establishing an in vivo wound infection model on a host induced by pathogens. Preferably, the host is a vertebrate. More preferably, the host is one or more types of fish. In certain embodiments, one or more types of fish include Medaka fish (or *Oryzias latipes*).

In an exemplary embodiment, the present device includes a multi-layered structure for culturing both the host animal and pathogens of interest whilst conducting a bioassay on the wound infection model established on the host animal. The multi-layered structure includes a base layer, an intermediate host-pathogen interface layer, a bioassay layer, and a barrier layer.

In certain embodiments, the intermediate host-pathogen interface and bioassay layers are laterally arranged and sandwiched between the base and barrier layers.

In other embodiments, the intermediate host-pathogen interface and bioassay layers are stacked between the base and barrier layers.

In certain embodiments, the intermediate host-pathogen interface layer and bioassay layer communicate to form a continuous fluid flow system between multiple fluid flow channels of the bioassay layer and multiple channels of the intermediate host-pathogen interface layer.

In certain embodiments, multiple layers of the multi-layered structure are made of the same material.

In an exemplary embodiment, a flexible, bendable, biocompatible, and inert to biological and chemical reactions with any host animal, pathogens, biological or chemical agents to be tested or screened is used to form the multiple layers of the multi-layered structure.

In certain embodiments, the multiple layers, including the base layer, an intermediate host-pathogen interface layer, bioassay layer, and barrier layer of the multi-layered structure, are all made of polydimethylsiloxane (PDMS).

In other embodiments, the multi-layered structure can be made of different materials among different layers.

In certain embodiments, each of the multiple layers of the multi-layered structure is made by 3D printing or photolithography, and the multiple layers are assembled by plasma treatment.

In certain embodiments, each of the channels in the intermediate host-pathogen interface layer is configured to entrap the host animal at its undeveloped stage into a compartment with an extension with a decreasing cross-sectional area towards a direction opposite to a direction fluid flowing through the channels from the bioassay layer.

In certain embodiment, each of the channels in the intermediate host-pathogen interface layer is periodically curved to form a sinusoidal waveform-like structure, and the compartment is disposed substantially at each of “crest” and “trough” of each “sine wave”. “Crest” and “trough” of each “sine wave” in the context of describing a geometry of the channels in the present invention refer to each of the dispositions at where the periodic curvature of each channel reaches its maximum amplitude when the channel is configured substantially in a sinusoidal waveform-like structure.

In certain embodiments, a water-permeable inner sidewall is provided between the compartment and its adjacent periodically curved channel to form an entrapment of the host animal by separating the compartment from the channels while only allowing fluid and other substances which are penetrable to the water-permeable inner sidewall to flow into the compartment.

In certain embodiments, to facilitate the entrapment of the host animal into the compartment, a sufficiently low static flow of fluid is provided for the periodically curved channels such that the fertilized embryos of the host animal are securely entrapped into the compartment.

In certain embodiments, the fluid flow in the channels is maintained on average at about 100 μl $min^{-1}$ when the channels have an average cross-sectional diameter or width of about 1 mm.

In certain embodiments, the host animal in the compartment is incubated until reaching a larval stage prior to inducing a wound thereon.

In certain embodiments, the wound is induced on the skin of the host animal.

In certain embodiments, the skin at which the wound is induced is at a tail portion of the host animal.

In certain embodiments, the tail skin wound of the host animal is induced by a superficial wound cut.

In certain embodiments, the superficial wound cut is inflicted at the tail portion of the host animal, which is disposed of in the extension of the compartment at the smallest cross-sectional area. More specifically, the tail portion of the host animal is disposed of at the tip of the extension of the compartment.

In certain embodiments, the pathogens inducing the wound infection include *Pseudomonas aeruginosa* (*P. aeruginosa*).

A second aspect of the present invention provides a method for screening potential drug candidates for treating inflammatory diseases caused by pathogens. The method includes:

- providing a pathogenic infection in vivo model in a microfluidic-based device;
- applying a fluid containing the potential drug candidate to the in vivo model through one or more fluid channels of the microfluidic-based device;
- assessing therapeutic effects of the potential drug candidate on the inflammatory diseases of the in vivo model qualitatively and quantitatively; and
- comparing the qualitative and quantitative assessment results of the therapeutic effects of the potential drug candidate with those of a known therapeutic agent for treating the same inflammatory diseases on the same model to determine whether the drug candidate is a potential anti-inflammatory agent.

In an exemplary embodiment, the microfluidic-based device includes a multi-layered structure. The multi-layered structure includes at least a base layer, an intermediate host-pathogen interface layer, a bioassay layer, and a barrier layer, where the intermediate host-pathogen interface layer and the bioassay layer communicate with each other to form a continuous fluid flow system.

In certain embodiments, the intermediate host-pathogen interface and bioassay layers are laterally arranged and sandwiched between base and barrier layers.

In other embodiments, the intermediate host-pathogen interface and bioassay layers are stacked between the base and barrier layers.

In certain embodiments, the intermediate host-pathogen interface layer includes multiple channels, where each channel includes multiple compartments, and each compartment has an extension with a decreasing cross-sectional area towards a direction opposite to a direction of fluid flow from fluid channels of the bioassay layer to the multiple channels of the intermediate host-pathogen interface layer.

In certain embodiments, each of the channels in the intermediate host-pathogen interface layer is periodically curved to form a sinusoidal waveform-like structure, and the compartment is disposed substantially at each of crest and trough of each sinusoidal waveform.

In certain embodiments, said providing the in vivo model in the microfluidic-based device includes:

- entrapping fertilized embryos of the host animal into each of the compartments of the multiple channels of the intermediate host-pathogen interface layer by providing a water-permeable inner sidewall arranged between each of the compartments and its adjacent channel such that only fluid and substances penetrable to the water-permeable inner sidewall can pass through while the fertilized embryos of the host animal are entrapped in the compartment;
- hatching the fertilized embryos until the host animal reaches the larval stage;
- inducing a wound on the skin of a tail portion of the host animal through a tip section of the extension of the compartment; and
- introducing pathogens to the compartment to co-culture with the host animal in the same compartment to establish a wound infection on the skin of the tail portion of the host animal;
- monitoring the wound infection qualitatively and quantitatively to verify the establishment and assess the extent of wound infection.

In certain embodiments, the host animal is selected from a fish.

In one embodiment, the fish includes Medaka fish (or *Oryzias latipes*) and zebrafish (*Danio rerio*).

In certain embodiments, the pathogens include bacteria, viruses, fungi, protozoa, parasites, or other microbes, either pathogenic, non-pathogenic, or commensal.

In certain embodiments, the bacteria can be free-swimming (planktonic) individual cells or multicellular aggregates encased in an exopolymeric matrix (or biofilm matrix).

In certain embodiments, the assessment of the extent of wound infection established on the host animal includes performing bioassays of a plurality of cytokines involved in said wound infection, observing morphological, cellular composition, and genetic changes in the biofilm formed on the infected wound by the pathogens or at the infection region of the host animal, and quantifying the expression of biomarkers, genetic markers, and presence of metabolites relating to the biofilm formation or infection.

In certain embodiments, said applying the fluid containing the potential drug candidate to the in vivo model includes establishing a concentration gradient from the first fluid channel to the last fluid channel of the bioassay layer of the microfluidic-based device.

In certain embodiments, said assessing the therapeutic effects of the potential drug candidate on the inflammatory diseases of the in vivo model qualitatively and quantitatively includes:

- observing the morphological change of the biofilm formed by the pathogens under microscopy and/or through histology; and
- quantifying the expression of biomarkers specific to the biofilm formation on the infected wound of the host animal.

In one embodiment, the pathogens are selected from *P. aeruginosa*.

In one embodiment, the biofilm formed by *P. aeruginosa* expresses a specific biomarker that scavenges iron from the host animal or the surrounding fluid in the compartment.

In one embodiment, the specific biomarker of the biofilm formed by *P. aeruginosa* is pyoverdine.

In one embodiment, the expression of pyoverdine is detectable under fluorescent microscopy.

In certain embodiments, said comparing the qualitative and quantitative assessment results of the therapeutic effects of the potential drug candidate with those of a known therapeutic agent for treating the same inflammatory diseases on the same model includes:

comparing the qualitative and quantitative assessment results of the therapeutic effects of the potential drug candidate with those of antibiotics, antimicrobials, anti-virulence agents, anti-biofilm agents such as inhibitors, dispersants, and disruptors, or any combination thereof, eradicating microbial infections due to the biofilm formation by the same species of pathogens on the same in vivo model, where the qualitative and quantitative assessment results include histological analyses and quantification of the local or systemic expression of specific biomarkers, genetic markers, and presence of metabolites relating to the biofilm formation or infection in the in vivo model.

The present invention is also applicable to showing the interaction between the host animal and one or more cell components of interest. In certain embodiments, the multi-layered structure of the present device may include a layer to which said one or more cell components is/are introduced for co-culturing with the host animal in the compartment, or the one or more cell components are introduced to the bioassay layer through the fluid channels communicating the corresponding channels of the intermediate host-pathogen interface layer according to the concentration gradient. Qualitative and quantitative assessments of various markers are performed according to certain embodiments of the present invention or any known methods used in studying the cellular, molecular, genetic, and/or chemical interactions between two different cell types. The therapeutic effects of the one or more cell components introduced to the infection model can also be assessed through the present device and methods described herein.

The present microfluidic-based device incorporating co-culturing of two different organisms in the same environment, establishing a wound infection model on a host, and qualitatively and quantitative assessment of effects of agents of interest at different concentrations on the wound infection in the same device also provides an insight into developing an in vivo model for use in basic researches and pre-clinical studies on different cellular, humoral, molecular and genetic interactions between two different organisms under the influence of the agents of interest.

This summary introduces a selection of concepts in a simplified form that is further described below in the Detailed Description. This summary is not intended to identify key features or essential features of the claimed subject matter, nor is it intended to be used as an aid in determining the scope of the claimed subject matter. Other aspects of the present invention are disclosed as illustrated by the embodiments hereinafter.

BRIEF DESCRIPTION OF DRAWINGS

The appended drawings, where like reference numerals refer to identical or functionally similar elements, contain figures of certain embodiments to illustrate further and clarify the above and other aspects, advantages, and features of the present invention. It will be appreciated that these drawings depict embodiments of the invention and are not intended to limit its scope. The invention will be described and explained with additional specificity and detail through the use of the accompanying drawings in which:

FIG. 1A schematically depicts a microfluidic platform for an in vivo wound infection model based on fish-microbe interactions according to certain embodiments of the present invention;

FIG. 1B shows an image of a continuous fluid flow system between multiple fluid flow channels (gradient generator) of the bioassay layer and multiple channels (channels for larvae-microbe co-culture) of the intermediate host-pathogen interface layer according to certain embodiments of the present invention;

FIG. 1C shows an image of introducing agents of interest through two fluid inlets to the multiple fluid flow channels of the bioassay layer and subsequently to multiple channels of the intermediate host-pathogen interface layer according to certain embodiments of the present invention;

FIG. 2A schematically depicts an establishment of an in vivo model in the microfluidic-based device, induction of wound infection, and assessment by microscopy according to certain embodiments of the present invention, and also shows a flowchart of different applications of the present wound infection in vivo model; Scale bar in the image: 1 mm;

Skilled artisans will appreciate that elements in the figures are illustrated for simplicity and clarity and have not necessarily been depicted to scale.

DETAILED DESCRIPTION OF THE INVENTION

It will be apparent to those skilled in the art that modifications, including additions and/or substitutions, may be made without departing from the scope and spirit of the invention. Specific details may be omitted so as not to obscure the invention; however, the disclosure is written to enable one skilled in the art to practice the teachings herein without undue experimentation.

The present disclosure provides the following detail to assist the understanding and enabling of the present invention, and it should not be considered to limit the scope of protection to those specifics described hereinafter.

Structure of Microfluidic-Based Device for Wound Infection In Vivo Model (MicroFish)

Figure 1D:
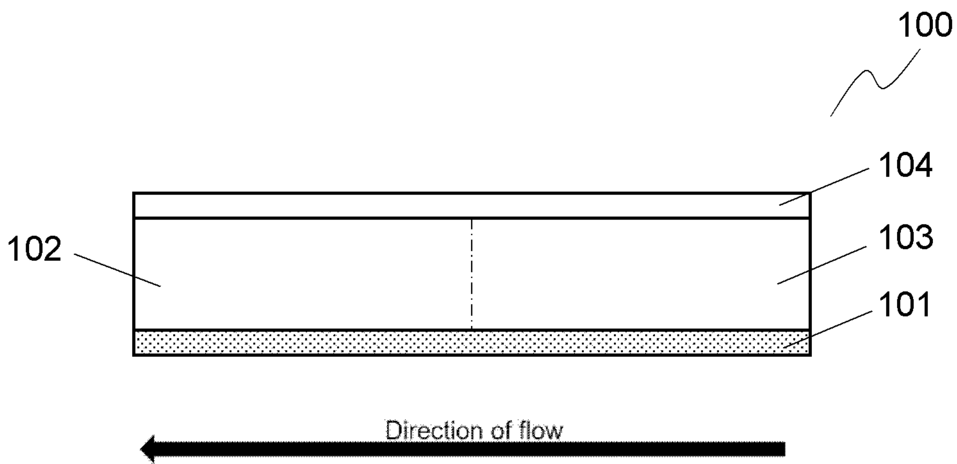
FIG. 1D schematically depicts a structure of the present device according to certain embodiments of the present invention.

Turning to FIGS. 1A and 1D, an integrated microfluidic device, is provided as a platform to show an interaction between microbes of interest and a desired in vivo model, fish, under defined conditions. Such a microfluidic-based platform for demonstrating fish-microbe interactions (MicroFish) 100 includes four key components: a bottom layer 101 in a dimension of 250-mm diameter and 2-mm thickness; an intermediate, multi-channel layer 102 as an interface for fish larvae-microbe co-culture, where each channel has a dimension of 1-mm height and 1-mm width; a bioassay layer 103 with a tree-like gradient generator to generate a number of drug gradient concentrations, e.g., eight channels with different drug concentrations in either an ascending or descending order; and a top barrier layer 104 to retain fluids. The microfluidic-based platform is made of polydimethylsiloxane (PDMS). Each layer is obtained from a master mold produced by 3D printing or standard photolithography. The layers made of PDMS can be permanently assembled by plasma treatment such as oxygen plasma surface activation.

Figure 7:
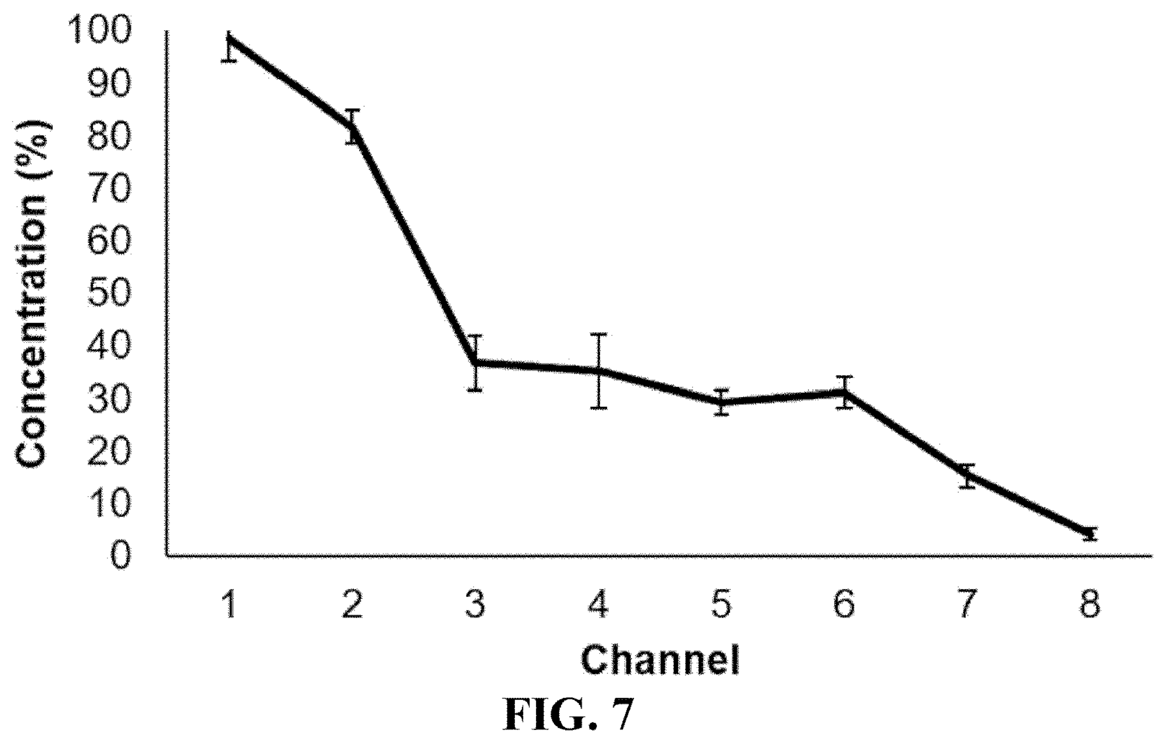
FIG. 7 shows a relative SYTO-9 dye concentration measured in eight channels at the intermediate host-pathogen interface layer against different initial dye concentrations applied to different corresponding fluid channels at the bioassay layer.

The performance stability of the gradient generator could be determined by the visualization of different colors of dyes (e.g., dark and light color dyes indicated by dark gray and light gray arrows, respectively, in FIG. 1B). It is observed that the change between the input concentration and output to the channels for fish larvae-microbe co-culture at the intermediate host-pathogen interface layer is not significant. To further quantify, an initial input flow rate of the gradient generator at 10 μl $min^{-1}$ is applied by a syringe pump as shown in FIG. 1C to two fluid inlets of the gradient generator. Sterile $ddH_2O$ and 30 μM SYTO-9 fluorescent dye (Invitrogen, USA) solutions are pumped into the MicroFish through the gradient generator, and the fluorescence intensity measurements of samples collected within the channels are obtained using a microplate reader (Tecan M200, Denmark). The relative concentrations of the fluorescent dye measured at eight different channels for fish larvae-microbe co-culture at the intermediate host-pathogen interface layer are shown in FIG. 7. FIG. 1D (not in actual proportion) illustrates one configuration of the microfluidic-based device, which is a multi-layered structure including the four key components as described hereinbefore. Although the multi-channel layer 102 for co-culturing the fish and microbes of interest are arranged substantially side-by-side at the same layer level as the bioassay layer 103 in this embodiment, it should be understood that the two layers can also be assembled as different layers adjacent to each other, as long as a continuous fluid flow between the two layers at a designated flow rate is provided.

Establishment of Fish-Microbe Co-Culture and Tail Wound on Fish in the MicroFish A tail-wound infection model is established using the Medaka fish and opportunistic *Pseudomonas aeruginosa* in the microfluidic-based device as described herein. Medaka fish is a model organism commonly used to study developmental biology and infection, as its genetic homology, organogenesis, and immune system are highly similar to that of humans. Other possible candidate for the host animal similar to humans in terms of those attributes mentioned above is zebrafish.

*P. aeruginosa* is a common pathogen that colonizes human wounds and fish. Hence, it is selected as a pathogen to induce wound infection in the fish model in order to demonstrate the high applicability and relevance of the present invention in clinical and aquaculture settings. In vivo bacterial infections on live animals are of clinical relevance, and their research can be highly translatable to human infections.

Figure 2B:
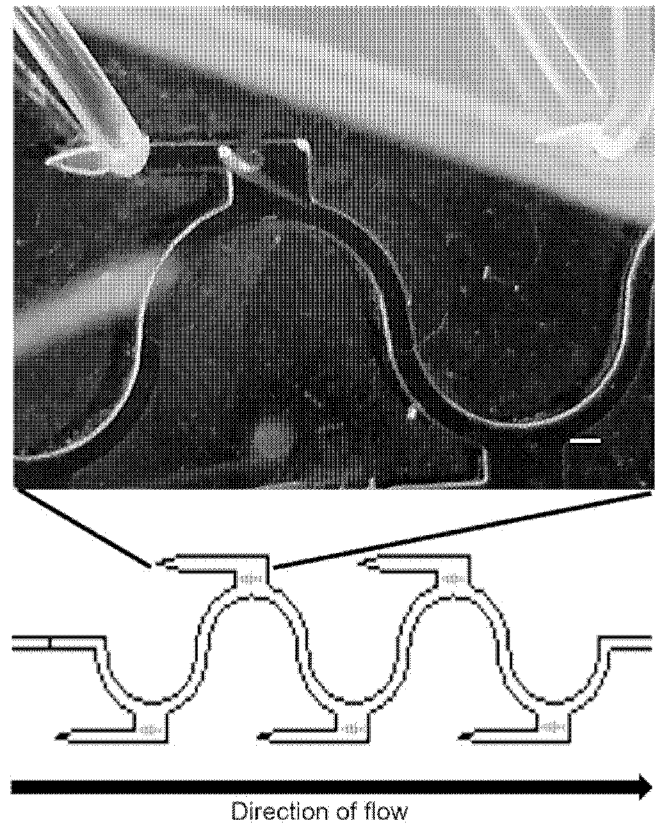
FIG. 2B shows an image and a schematic diagram of inducing wound infection at a tail portion of an in vivo model according to certain embodiments of the present invention.
Figure 8:
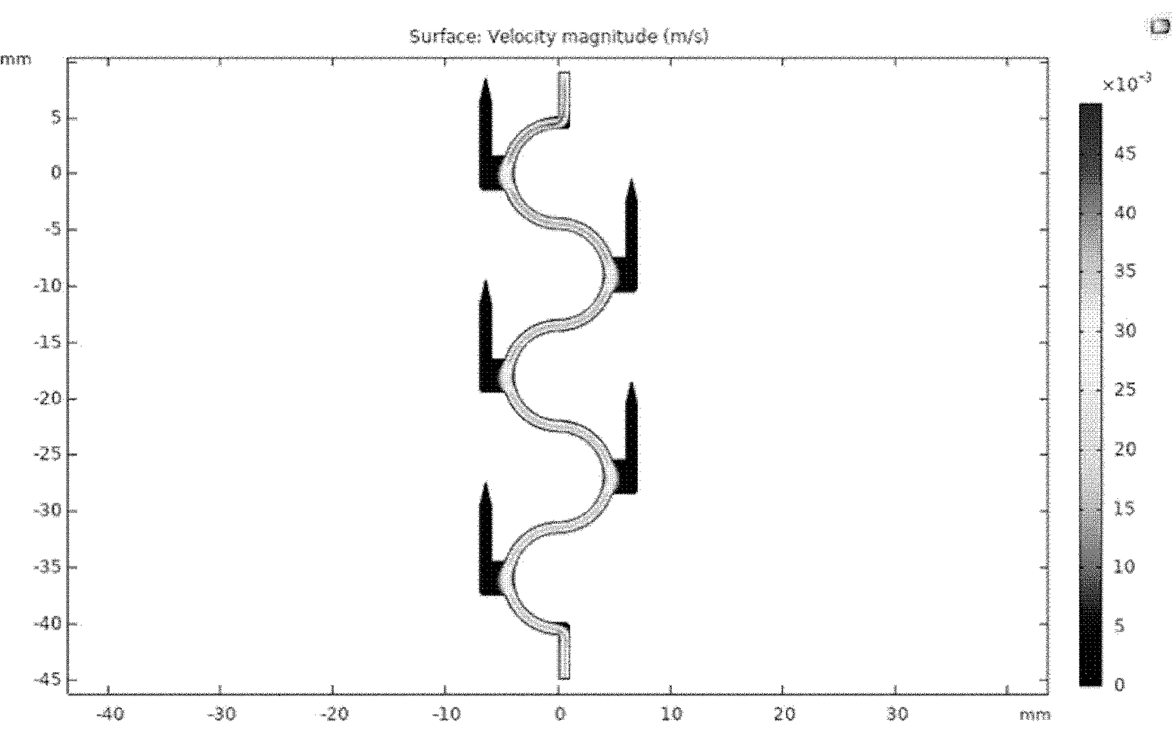
FIG. 8 shows a flow rate distribution map at individual channels of the intermediate host-pathogen interface layer of the present invention using COMSOL simulation.

Turning to FIG. 2A, for the selected host animal to develop in the MicroFish, a continuous flow of freshwater at 100 μl $min^{-1}$ is preferably used to transfer each fertilized egg into individual compartments (or entrapments) within the MicroFish. Due to the curvature of the channel leading to each entrapment (periodically curved in a shape like a sinusoidal waveform where at each crest or trough of each sinusoidal waveform is disposed with said entrapment), the eggs will be pushed towards the inner sidewall and into the entrapments. The relatively low static flow in the area will cause the eggs to remain within the entrapments (a designated flow rate distribution model is shown in FIG. 8, in which different color grayscales represent different flow rates in the MicroFish, especially at different parts of the sinusoidal waveform-shaped channels and their corresponding entrapments for fish-microbe co-culture). In certain embodiments, the depth of the entrapment is approximately 1 mm or more for hatching the fertilized eggs.

Figure 2C:
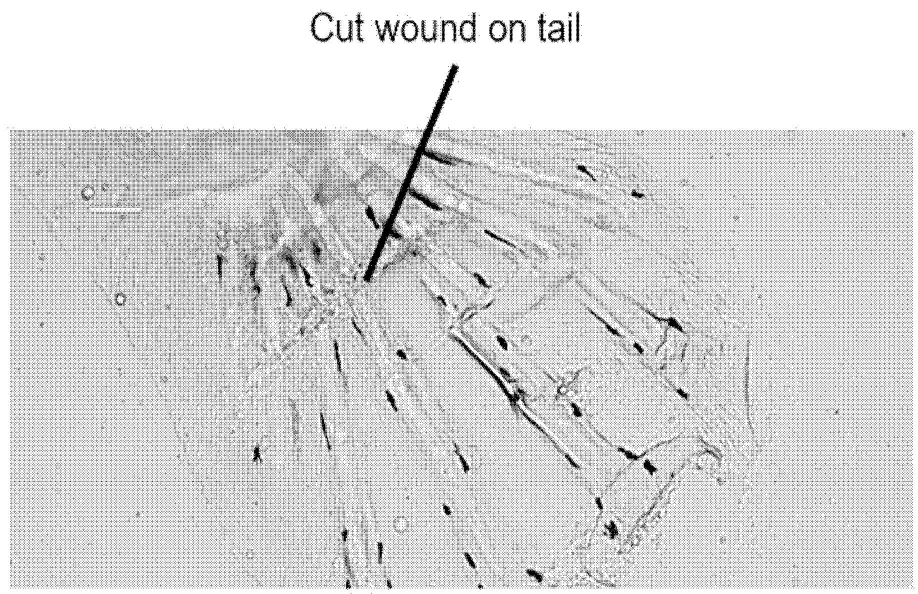
FIG. 2C shows an image of the wound inflicted on the in vivo model (fish) tails by the procedures as shown in FIGS. 2A and 2B.

After the fertilized eggs are hatched into fish larvae in the entrapments, the fish will be fed by injecting food through the injection port for 48 hrs. The fish larvae are incubated in freshwater within each channel for 3 days post fertilization (d.p.f). A superficial wound cut is inflicted by an injection needle on the fish tail to establish pathogenic infections in the MicroFish (as in the images of FIGS. 2B and 2C, respectively). The established co-culture system and tail wound on fish model in the MicroFish has a wide range of applications, including studying host-microbe interaction, in vivo evaluation of the efficacy of antimicrobials against microbial infection, and routine screening of antibiotic or antibiofilm agent and its efficacy in microbial clinical isolates, etc.

Figure 3A:
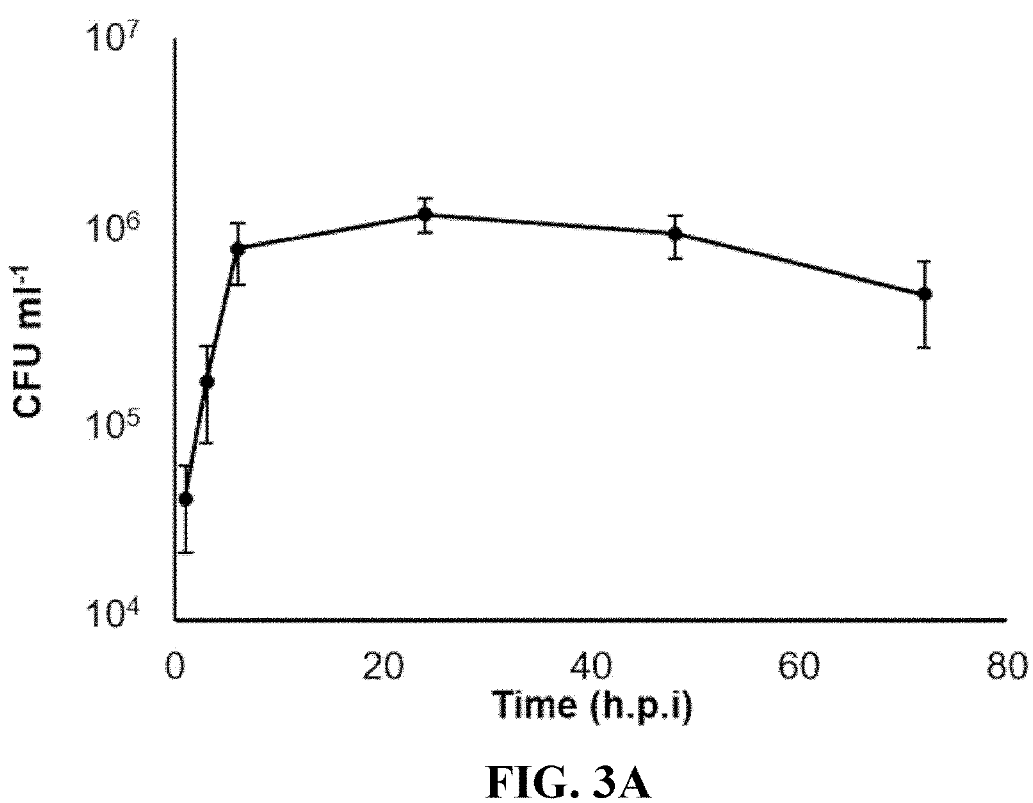
FIG. 3A shows the change of viable cell counts (CFU of wild-type *P. aeruginosa* or "PAO1") on an infected wound induced on tails of the in vivo model (fish) according to certain embodiments of the present invention over time; h.p.i.=hours post-infection.
Figure 3B:
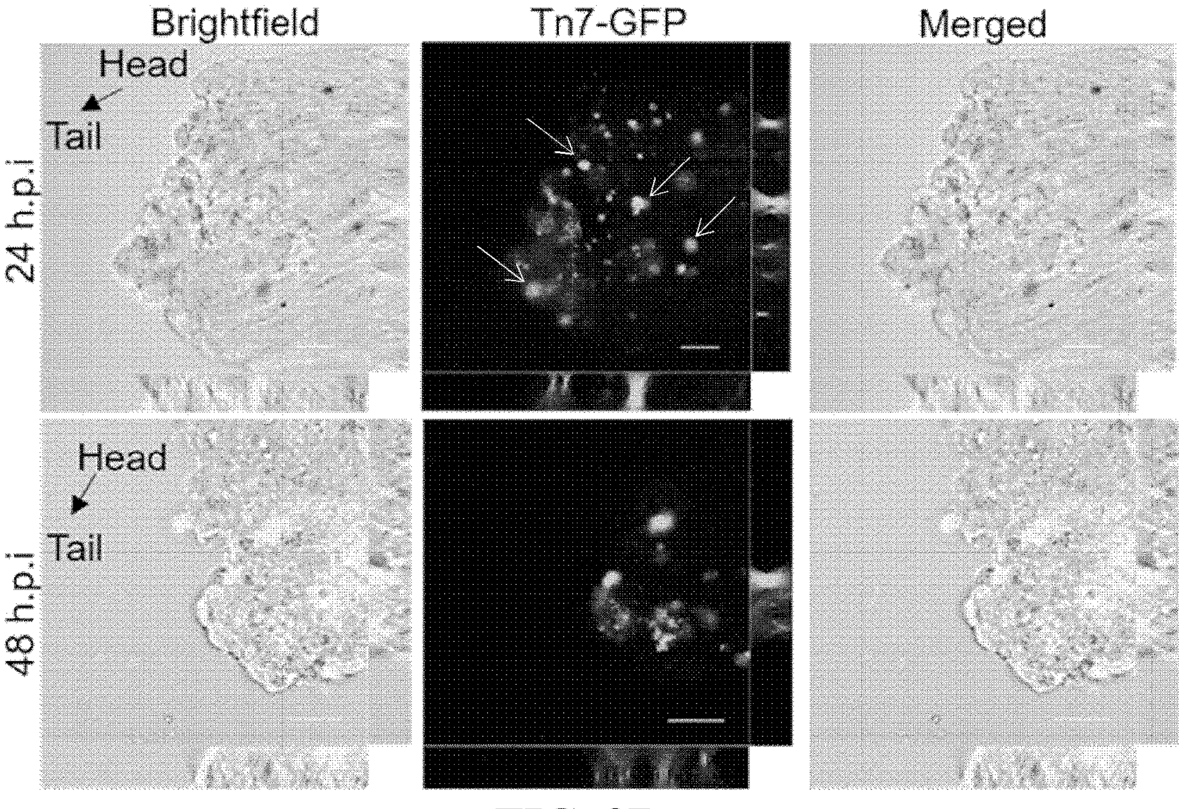
FIG. 3B shows bright-field and fluorescence images of GFP-tagged *P. aeruginosa* colonization on tail wounds over 24 h.p.i. (top row) and 48 h.p.i. (bottom row); scale bar: 50 μm.

Turning to FIG. 3A, to verify and monitor the development of wound infection in the fish model induced by *P. aeruginosa*, viable cell counts from colonies formed at the wound region over time (1, 3, 6, 24, 48, and 72 h.p.i.) are recorded. The result demonstrates that the maximum CFU ($\sim 1\times10^6$ CFU $ml^{-1}$) is reached at 6 h.p.i. and remains substantially constant till 72 h.p.i. To demonstrate localization of *P. aeruginosa* at the wound region, the wild-type *P. aeruginosa* (PAO1) is tagged with a constitutively-expressed gfp gene (Tn7-gfp) before introducing to the tail wound of the Medaka fish. Phase-contrast and green fluorescence microscopy on the entrapments 24 and 48 h.p.i. is used to visualize cell aggregates around the wound region of the fish by the PAO1/Tn7-gfp and detect the green fluorescence signals from the expression of Tn7-gfp, to verify the localization and formation of cell aggregates at the wound region by *P. aeruginosa* (FIG. 3B).

Figure 9:
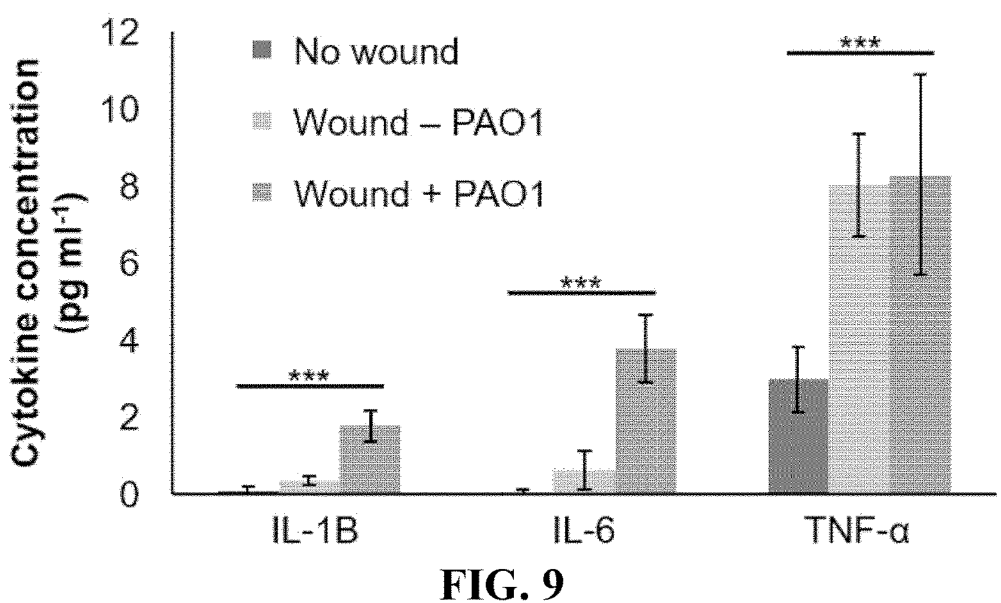
FIG. 9 shows ELISA results of selected pro-inflammatory cytokines in an in vivo model (Medaka fish) with and without *P. aeruginosa* (PAO1) infection; ***P<0.001.

An enzyme-linked immunosorbent assay (ELISA) is performed to verify that the tail wound inflicted in the fish model, according to certain embodiments of the present invention, will trigger immune responses by measuring the expression level of certain innate immunity cytokines such as IL-1B, IL-6, and TNF-α, which are pro-inflammatory cytokines that are commonly upregulated during infections, with multiple paralogues in many animal species. Different treatment groups (no wound; wound without PAO1 infection; and wound infected by PAO1) are compared, and the ELISA results are shown in FIG. 9. The results show that these cytokines are significantly upregulated in the wound infection fish models, suggesting that the immune system is activated normally in response to the presence of bacterial infection in the wound region.

Formation and Characterization of Biofilm and Biofilm-Mediated Wound Infection on Fish Model Induced by Bacteria Since the National Institutes of Health estimates that 80% of bacterial infections are mediated by biofilms (Davies D., 2003), it will be more convincing to understand whether there is biofilm formation by *P. aeruginosa* and the role of the biofilm in bacterial colonization and establishment of wound infection on the fish tail.

Figure 4A:
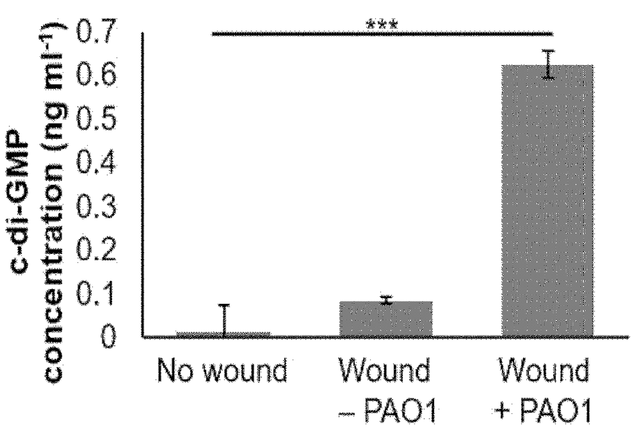
FIG. 4A shows the expression of a marker (c-di-GMP) quantitatively at tails of the in vivo model under different treatment groups (no wound; wound without PAO1; and wound with PAO1) according to certain embodiments of the present invention; ***$P<0.001$.

Since a ubiquitous bacterial secondary messenger, c-di-GMP, positively regulates biofilm formation in Gram-negative bacteria, including *P. aeruginosa*, this can be an indicator of the presence of biofilm formed by *P. aeruginosa* in the wound region of the fish tail. FIG. 4A shows a quantitative analysis by ELISA on the cells around the wound region. The results show that c-di-GMP level is elevated in the fish group with tail wound and co-culture with PAO1, compared to a minimal level of c-di-GMP expression and substantially no c-di-GMP expression in the tail wound group without PAO1 and healthy fish group, respectively, which confirms that the biofilm formation is due to the presence of *P. aeruginosa.*

Figure 4B:
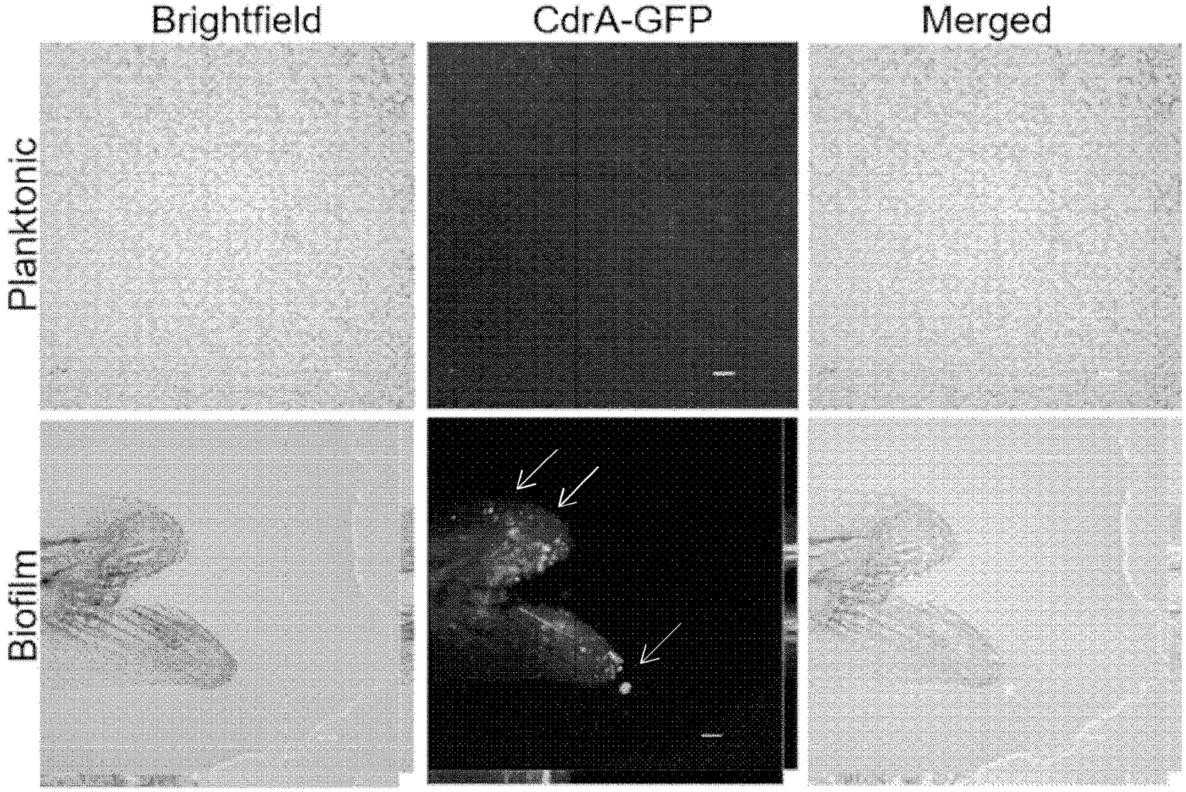
FIG. 4B shows bright-field and fluorescence images of GFP-tagged PAO1 individual cells (top row: planktonic) and or cell aggregates (bottom row: biofilm) in the culturing medium and at around the wound region of the tails of the in vivo model, respectively, after 48 h.p.i.; scale bar: 50 μm.

Turning to FIG. 4B, a c-di-GMP transcriptional fusion biomarker, $p_{cdra}$-gfp, or its biofilm product, CdrA, are used to observe the localization of *P. aeruginosa* in the biofilm formed at the wound region of the fish tail. The wild-type *P. aeruginosa* with a GFP tagged to CdrA (PAO1/$p_{cdra}$-gfp) is introduced to the wound of the fish tail. The green fluorescence signals observed under a fluorescent microscope reveal that the expression level of CdrA is higher around the wound region (bottom row), whereas the unbound or free-floating (planktonic) bacteria are not detected with significant or observable green fluorescence signals (top row). Both c-di-GMP levels and CdrA expression corroborate and confirm the correlation between c-di-GMP levels and the wound infections on fish tail.

Figure 4C:
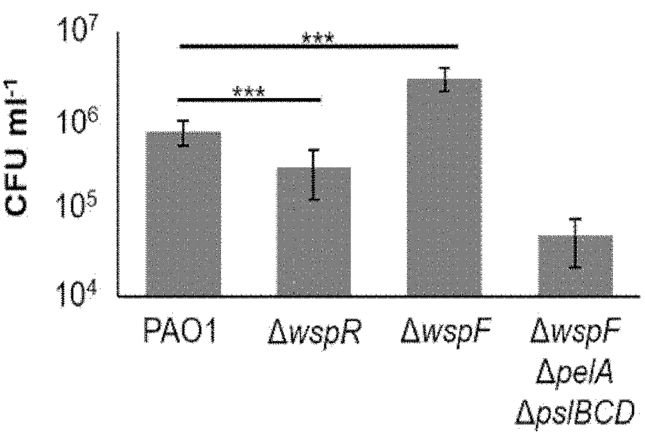
FIG. 4C shows viable cell counts from biofilms formed by different *P. aeruginosa* mutants (ΔwspR; ΔwspF; ΔpelAΔpslBCD) on the infected wound of the in vivo model according to certain embodiments of the present invention; ***$P<0.001$.
Figure 4D:
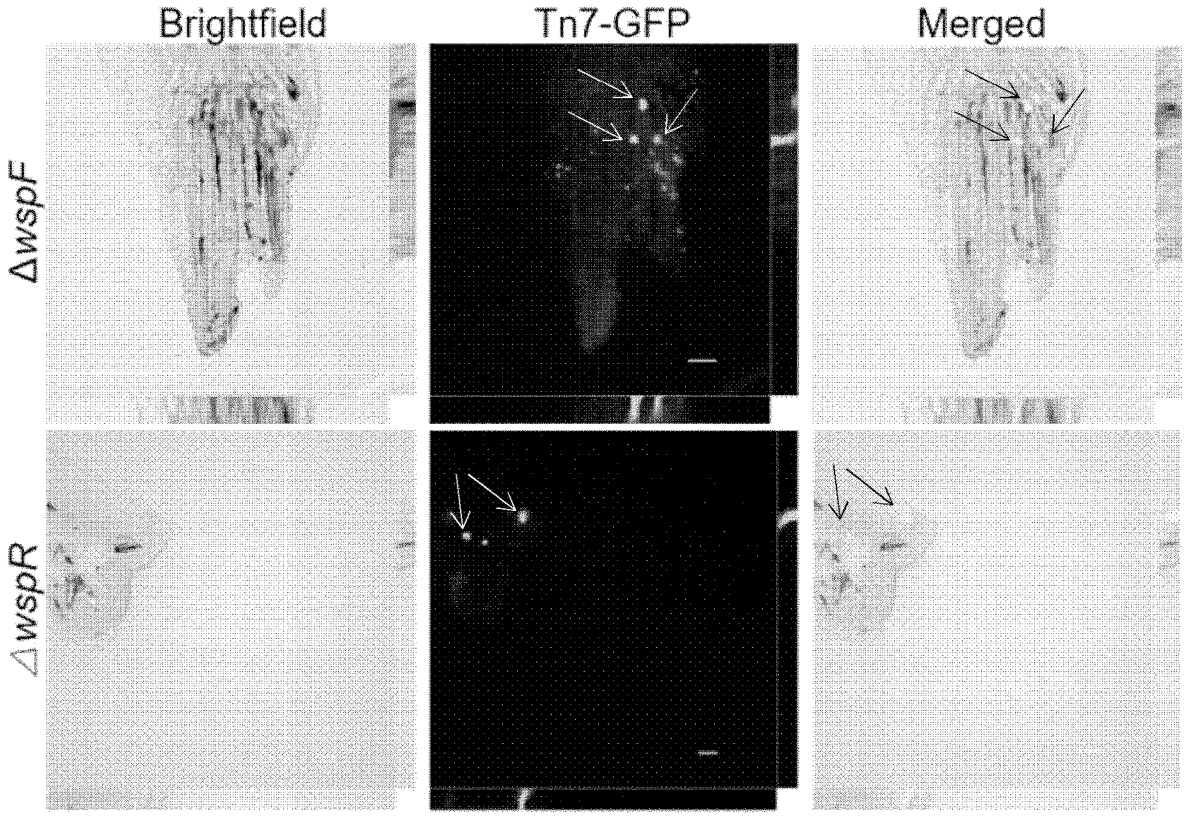
FIG. 4D shows bright-field and fluorescence images of cell aggregates from the biofilms formed around the wound region of the tails of the in vivo model by two different *P. aeruginosa* mutants (top row: ΔwspF; bottom row: ΔwspR)
Figure 4E:
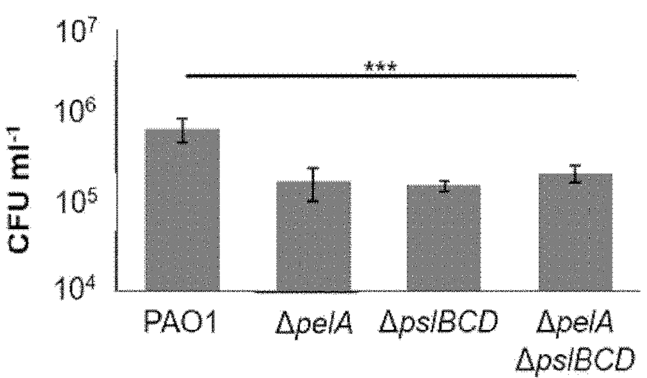
FIG. 4E shows viable cell counts from biofilms formed by different *P. aeruginosa* mutants (ΔpelA, ΔpslBCD, and ΔpelAΔpslBCD) and wild type *P. aeruginosa* (PAO1) on an infected wound of the in vivo model according to certain embodiments of the present invention; ***$P<0.001$.

Diguanylate cyclase WspR, a conserved GGDEF domain-containing response regulator in the c-di-GMP synthesis of Gram-negative bacteria, including *P. aeruginosa*, and inducing biofilm formation, also plays a crucial role in wound infection. To demonstrate the significance of this regulator in wound infection, a WspR-deficient mutant, ΔwspR, is used to induce biofilm formation at the fish tail wound and compare it with that formed by the wild type *P. aeruginosa* (PAO1). At the same time, a mutant with overexpression of WspR. ΔwspF, which results in de-repression on WspR expression, is used in the same study. Quantitative (FIG. 4C) and qualitative (FIG. 4D) results show that bacterial colonization in ΔwspR mutant is weaker than both wild-type (PAO1) and ΔwspF mutant; ΔwspF mutant has the highest level of colonization among the three. In the same test, a biofilm matrix deficient mutant (ΔpelAΔpslBCD) is also used to induce biofilm formation at the wound region of the fish tail to demonstrate the correlation between normal biofilm growth and wound infection by *P. aeruginosa*, since *P. aeruginosa* produces and secretes three known exopolysaccharides (Pel, Psl, and alginate), adhesion protein (CdrA), and extracellular DNA (eDNA) in the formation of biofilm matrix. It is not surprising that the colonization level in terms of viable cell counts is lower than any of the other three groups (FIG. 4C). FIG. 4E further reveals that lacking any one or all of these exopolysaccharides (i.e., Pel, Psl, or both) in *P. aeruginosa* fails to establish a biofilm-mediated wound infection model.

Another biomarker, pyoverdine, is also crucial to the biofilm-mediated wound infection on the fish tail. It is an iron siderophore to scavenge iron from the surroundings or host cells. It is also a good indicator of the effectiveness of a potential anti-biofilm agent because pyoverdine itself is self-fluorescent (Ex: 405 nm; Em: 460 nm), and the emission wavelength is similar to that of DAPI dye, allowing an easy and quick detection and monitoring by fluorescent microscopy or UV light devoid of artificial GFP-based biosensors into bacteria or dyes to stain the samples and extraction of samples for downstream analysis.

Figure 5A:
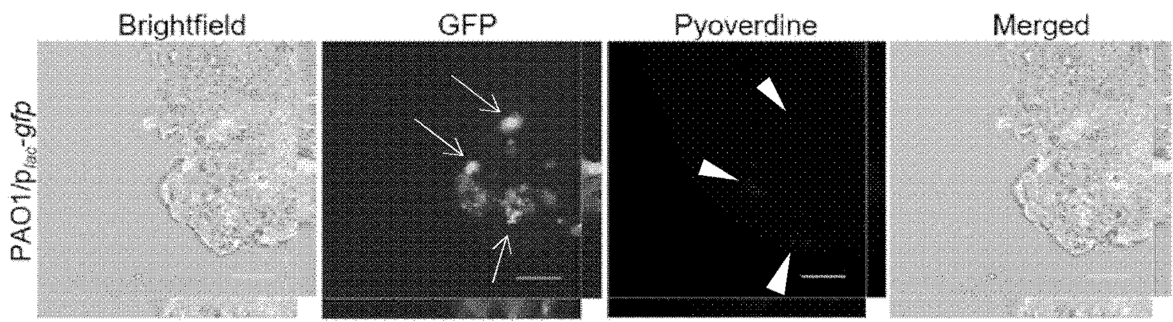
FIG. 5A shows an expression of a biomarker (pyoverdine) of biofilm-mediated wound infection in the in vivo model induced by GFP-tagged wild type *P. aeruginosa* (PAO1/$p_{lac}$-gfp); Scale bar: 50 μm.
Figure 5B:
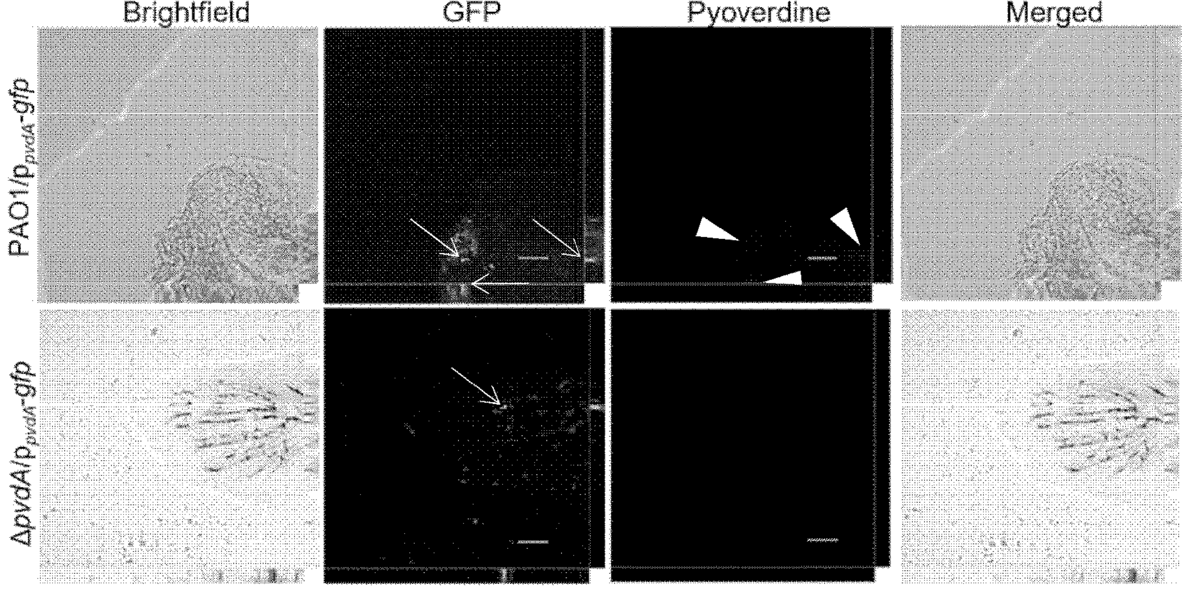
FIG. 5B shows an expression of a biomarker (pyoverdine) of biofilm-mediated wound infection in the in vivo model induced by two *P. aeruginosa* mutants (top row: PAO1/$p_{prdA}$-gfp; bottom row: ΔpvdA/$p_{pvdA}$-gfp); Scale bar: 50 μm.
Figure 5C:
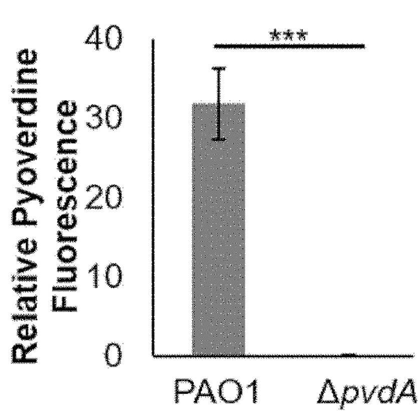
FIG. 5C shows pyoverdine expression from colonies of biofilm with wound infection induced by wild-type (PAO1) and a pyoverdine-deficient *P. aeruginosa* mutant (ΔpvdA); ***P<0.001.
Figure 5D:
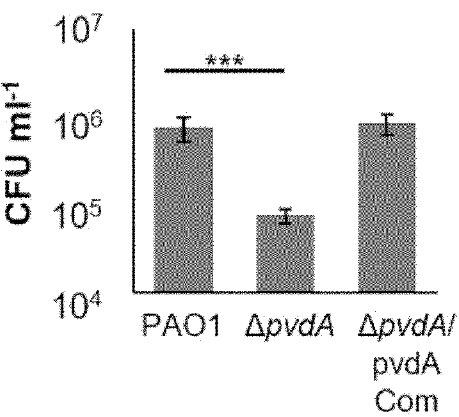
FIG. 5D shows viable cell counts with pyoverdine expression from biofilm with wound infection induced by wild-type (PAO1), a pyoverdine-deficient *P. aeruginosa* mutant (ΔpvdA), and the pyoverdine-deficient *P. aeruginosa* mutant compensated by ΔpvdA expression (ΔpvdA/pvdA Com); ***P<0.001.

In FIG. 5A, the localization of pyoverdine at the wound region of the fish tail is detected directly from the MicroFish under a fluorescent microscope and UV light (indicated by different types of arrows in green fluorescence and UV light images, respectively), in which the green fluorescence comes from the GFP-tagged PAO1 for co-localization of both bacterial cells and pyoverdine expression in the biofilm sample. In FIG. 5B, a higher GFP signal is detected in the pvdA-gfp transcriptional fusion biosensor-containing bacterial sample (top row: PAO1/PpvdA-gfp) than planktonic cells (bottom row: ΔpvdA/PpvdA-gfp). As a negative control, the pyoverdine-deficient (ΔpvdA) mutant shows no relative pyoverdine fluorescence compared to the wild-type (PAO1), suggesting the positive correlation between localization of pyoverdine and upregulation of pyoverdine synthesis genes (FIG. 5C). FIG. 5D further suggests that the ΔpvdA mutant cannot effectively establish wound infection in lower viable cell counts than the wild-type (PAO1) and the pyoverdine-deficient mutant compensated with the pyoverdine gene ΔpvdA/pvdA Com (ΔpvdA/$p_{lac}$-pvdA).

Figure 5E:
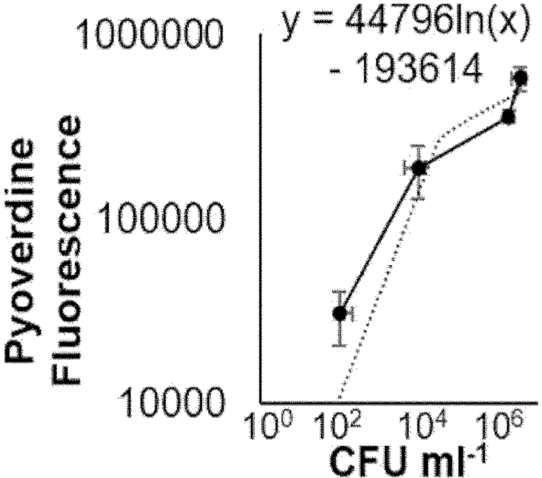
FIG. 5E shows a correlation between pyoverdine expression and viable cell counts from biofilms formed by PAO1.

To demonstrate the correlation between pyoverdine expression and viability of biofilm, biofilm morphological change against different concentrations of an antibiotic, ciprofloxacin, at 0, 0.05, 1, 5, 10 μg $ml^{-1}$ added into the co-cultures of the fish-microbe model is observed by measuring the pyoverdine fluorescence signals under confocal laser scanning microscopy (CLSM) with ImageJ. FIG. 5E shows a standard curve of viable cell counts (CFU) against pyoverdine fluorescence level. The standard curve is reflected by the following equation:

$$y=44796In(x)-193614 \quad (1)$$

From the curve, it indicates that the pyoverdine expression level positively correlates to biofilm viability. In other words, the higher the ciprofloxacin concentration is, the lower the pyoverdine expression, revealed by lower biofilm viability.

In view of different correlation studies on pyoverdine expression, it is suggested that pyoverdine is a suitable biomarker for *P. aeruginosa* biofilm-mediated wound infections.

Use of Microfluidic-Based In Vivo Wound Infection Model in Evaluation of Combinational Drug Efficacy To assess the drug assay component and clinical utility of the MicroFish platform for screening and test antimicrobial compounds against biofilm infection in the fish wound model, efficacy of combinatorial treatment of an anti-biofilm agent and an antibiotic is evaluated by the MicroFish. Anti-biofilm agents would disperse or disrupt biofilms and release entrapped biofilm cells for antibiotics to eradicate effectively. We treated the co-cultures with a synergistic combination of sodium nitroprusside (SNP) and ciprofloxacin antibiotic as a proof of concept. SNP is nitric oxide (NO) donor that downregulates c-di-GMP signaling and promotes biofilm dispersal, while ciprofloxacin is a commonly used fluoroquinolone antibiotics to treat *P. aeruginosa* infections.

Figure 6A:
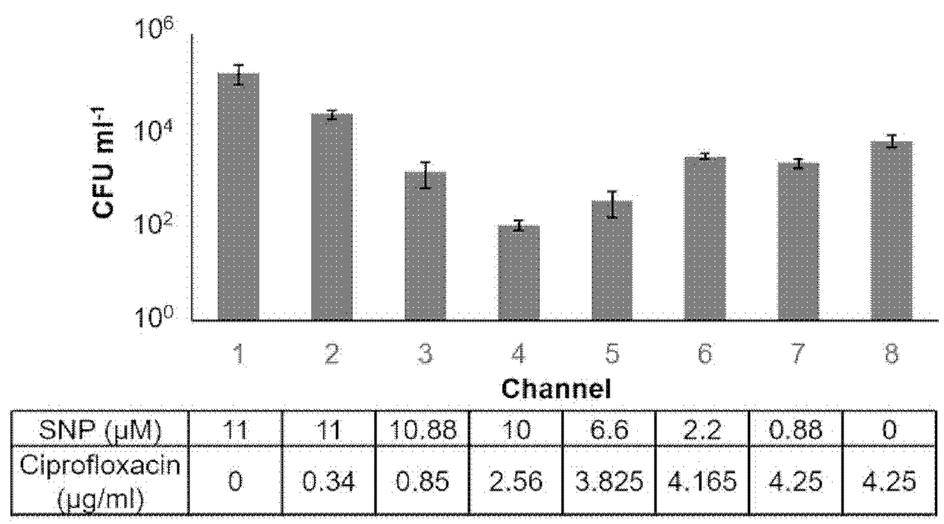
FIG. 6A shows viable cell counts from biofilm with wound infection induced by PAO1 after a combinational treatment of sodium nitroprusside (SNP) and ciprofloxacin antibiotics at different concentrations.
Figure 6B:
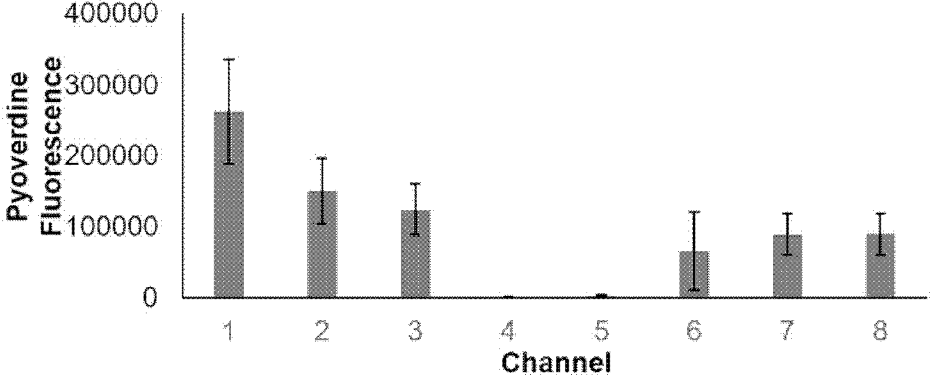
FIG. 6B shows the expression level of pyoverdine from biofilm with wound infection induced by PAO1 after a combinational treatment of sodium nitroprusside (SNP) and ciprofloxacin antibiotics at different concentrations.

FIG. 6A shows that SNP-ciprofloxacin combinatorial therapy can reduce the number of viable bacteria in the biofilm, where 10 μM SNP and 2.56 μg $ml^{-1}$ ciprofloxacin combinatorial concentrations are the most effective in eradicating biofilms among the eight tested combinations. This result corresponds to reducing pyoverdine levels in the biofilm as shown in FIG. 6B.

Figure 6C:
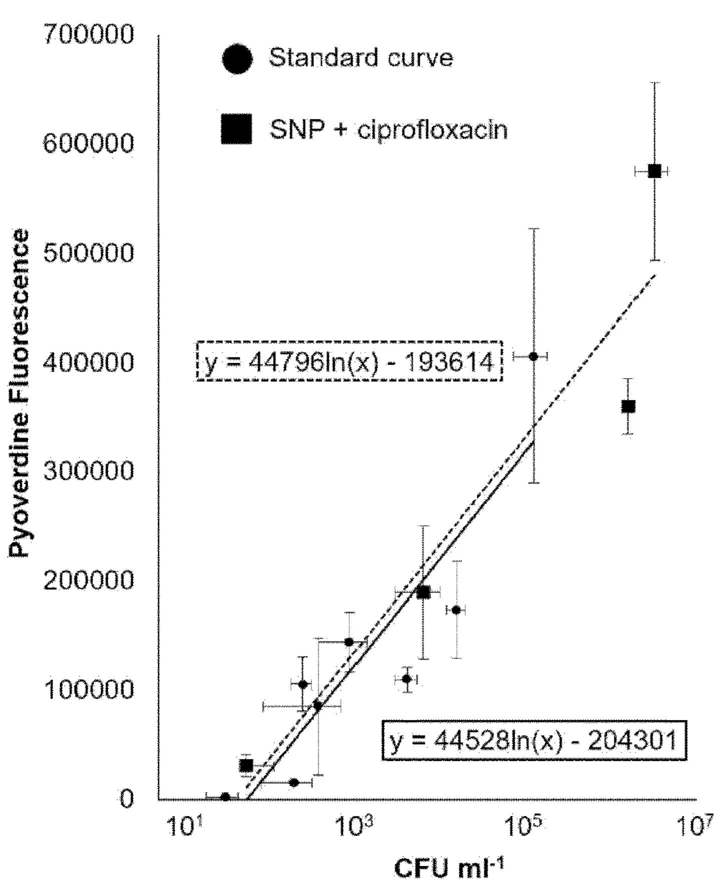
FIG. 6C shows a correlation between pyoverdine expression and viable cell counts from biofilms formed by PAO1 after the combinational treatment of SNP and ciprofloxacin compared to a standard curve (the correlation as shown in FIG. 5E)

To determine whether SNP-ciprofloxacin combinatorial therapy has synergistic effect on biofilm-mediated infections, Fractional Inhibitory Concentration (FIC) index is measured, and the plot of FIC index is compared with the standard curve as shown in FIG. 5E (for the correlation between pyoverdine fluorescence and biofilm viability under a ciprofloxacin monotherapy). Compared with ciprofloxacin monotherapy, FIG. 6C shows that much lower ciprofloxacin concentrations are used in the combinatorial therapy with SNP which is more effective in eradicating biofilms. It also shows the standard curve in FIG. 5E demonstrating the positive correlation between the pyoverdine level and CFU accurately reflects the viable cell counts in FIG. 6A, verifying the reliability of using pyoverdine as a fluorescent biosensor to monitor biofilm-mediated infections and further evaluate the antimicrobial efficacy of unknown agents in terms of their accuracy and sensitivity. Similar to the standard curve in FIG. 5E, the plot in FIG. 6C can be reflected by the following equation:

$$y=44528In(x)-204301 \quad (2)$$

The following section provides detail on how to establish different in vivo models and conduct certain assessments according to certain embodiments of the present invention, which is to assist the illustration of enabling certain embodiments, but it should not be considered to limit the scope of the invention by the detail provided hereinafter:

Examples (A) Fish Cultures

Wild-type Medaka fish were used for the experiments, where mixed male and female populations of animals were reared in treated freshwater (salinity 3 psu, pH 6.5, temperature 26-28° C.) at a ratio of 1 fish to 1 L water. The light rhythm was kept at a light-dark ratio of 14 hrs:10 hrs. For food, the animals were fed with dry material food (Marubeni Nisshin Feed, Japan) and *Artemia nauplii* three times a day (twice by dry food and once by *Artemia*), and the fishes should consume the quantity of food in 3 mins.

The fertilized eggs were obtained by natural spawning and maintained in fresh sterile artificial water with salinity around 10 psu (medium renewed every two days) at 26-28° C. The eggs were treated gently with emery paper to remove the long sticky villus around the eggs and separate them into single ones. After separation, each egg was placed in sterilized water with salinity=10 psu at 26-28° C. for 8-9 days.

After hatching, larvae fishes were fed with dry powder food mixed with rotifers (*Brachionus rotundiformis*) for 2-3 days.

(B) Bacterial Cultures

The bacterial strains and plasmids used in this study were listed in Table 1. *E. coli* DH5a strains were used for DNA conjugation. Luria-Bertani (LB) medium (Difco, Becton Dickinson and Company. USA) was used to cultivate *E. coli* and *P. aeruginosa* strains for bacterial growth. Bacterial strains were inoculated in 2 ml LB medium with appropriate antibiotics for plasmid maintenance overnight at 37° C. with 200 rpm shaking.

TABLE 1

| Strain/plasmid | Description | Source/ Reference |
|---|---|---|
| | *P. aeruginosa* | |
| PAO1 | Prototypic nonmucoid wild-type strain | Holloway et al., 1986 |
| ΔwspF | wspF knockout of PAO1 constructed by allelic exchange | Rybtke et al., 2012 |
| ΔwspR | wspR knockout of PAO1 constructed by allelic exchange | Liu et al., 2021 |
| ΔpvdA | pvdA knockout of PAO1 constructed by allelic exchange | Visca et al., 1994 |
| ΔpvdA/$p_{lac}$-pvdA | $Tc^r$, ΔpvdA containing the $p_{lac}$-pvdA plasmid | Present disclosure |
| PAO1/$p_{lac}$-gfp | $Strep^r$, PAO1 containing the Tn7-transposon ($p_{lac}$-gfp), with constitutively expressed GFP | Lambertsen et al., 2004 |
| PAO1/$p_{cdrA}$-gfp | $Gm^r$, PAO1 containing the $p_{cdrA}$-gfp vector | Chua et al., 2013 |
| PAO1/$P_{pvdA}$-gfp | $Tc^r$, PAO1 containing the $p_{pvdA}$-gfp transcriptional fusion biosensor | Chen et al., 2015 |
| ΔpvdA/$p_{pvdA}$-gfp | $Tc^r$, ΔpvdA containing the $p_{pvdA}$-gfp transcriptional fusion biosensor | Present disclosure |
| ΔwspF/$p_{lac}$-gfp | $Strep^r$, constitutively expressed GFP in ΔwspF mutant | Present disclosure |
| ΔlaslΔrhll/$p_{lac}$-gfp | $Strep^r$, constitutively expressed GFP in ΔlaslΔrhll mutant | Present disclosure |
| | Plasmid | |
| $p_{lac}$-pvdA | $Tc^r$ complementation plasmid, expresses PvdA, the ornithine hydroxylase | Olucha et al., 2011 |
| pRk600 | $Cm^r$; ori ColE1 RK2-$Mob^+$ RK2-$Tra^+$; helper vector for conjugation | Kessler et al., 1992 |
| $p_{lac}$-gfp | $Ap^r$ $Strep^r$; Tn7 transposon vector carrying the $p_{lac}$-gfp fusion | Barnes et al., 2008 |
| $p_{cdrA}$-gfp | $Ap^r$ $Gm^r$; pUCp22 carrying the $p_{cdrA}$-gfp fusion | Liu et al., 2021 |
| $p_{pvdA}$-gfp | $Ap^r$ $Tc^r$; Tn7 transposon vector carrying the $p_{pvdA}$-gfp fusion | Chua et al., 2014 |

(C) Fabrication of MicroFish

CAD software was used to design the microfluidic platform as 4 components. First, there was a base layer with a diameter of 25 cm and a thickness of 2 mm. Second, the middle channel layer of fish larvae-microbe co-culture, in which the height and width of the channel were 1 mm. The third layer generated various drug concentrations through a tree-shaped gradient generator composed of 2 inlet channels and 8 output channels. The length and width of all channels were 1×1 mm. A final barrier layer was added on top to retain fluids. As previously described, each layer was obtained from a master mold produced by 3D printing or standard photolithography, as previously described[7]. Briefly, polydimethylsiloxane (PDMS) devices were made by double-casting. PDMS was prepared using the Sylgard 184 Silicone Elastomer Kit (Dow Corning, USA) via a thorough mixing of the base resin and curing agent in a ratio of 10:1 (w/w). Holes were made on the inlet and outlet channels to join tubes to the device. The layers were adhered together with PDMS and cured under 70° C. for at least 2 hours. The device was sterilized with 70% ethanol before use.

(D) Calibration of Gradient Generator

The ddH2O and 1% (33.4 μM) SYTO-9 fluorescent dye (Invitrogen, USA) were pumped into the gradient generator through separate inlets with a syringe pump (New Era Pump Systems, Farmingdale, USA) at 30 μl $min^{-1}$. Samples were collected from the 8 outlets for fluorescence density measurement with a microplate reader (Tecan, Infinite M1000 Pro, Switzerland). To visualize the gradient distribution generated in the device, blue and red food dyes were introduced together with the syringe pump, followed by image analysis.

(E) Establishment of Fish Model of Skin Infection

Fertilized Medaka eggs (total number=40) were pumped and placed into their respective channels at 100 μl $min^{-1}$ freshwater using the syringe pump (New Era Pump Systems, Farmingdale, USA). Fish/eggs culture media was pumped into the device at the speed of 0.03-0.05 μl $min^{-1}$ until the larvae fishes hatched. For surgery and infection with *P. aeruginosa*, the fishes were first anesthetized by injecting 0.015 μM anesthesia tricaine mesylate (MS-222 for short, Sigma-Aldrich, USA) into the entrapment via the injection port. A syringe needle (26G×1½", 0.45×13 mm, Terumo, Japan) was placed past the injection port to cut a skin wound (~100 μm) on the tails of the fish gently under a light stereomicroscope. The wound infection was established by pumping freshwater with *P. aeruginosa* ($1\times10^7$ cells $ml^{-1}$) into the device to expose the wound to bacterial colonization directly without flow. After 1 h.p.i for bacteria to colonize the wound surface, freshwater media flow (0.1 μl $min^{-1}$) by syringe pump was reinstated to wash away residual anesthetic and unbound bacteria. The washing procedures allowed the infection to establish over different time points. At the endpoint of the experiment, the fish were euthanized with an overdose of MS-222 (0.045-0.05 mM) (Sigma-Aldrich, USA) for 20-30 min until the fish's heart stopped beating.

(F) Epifluorescence Imaging of Biofilms on Fish Wounds

All the microscopy images of biofilms on fish wounds were captured by the Nikon Eclipse Ti2-E Live-cell Fluorescence Imaging System using 20× or 40× objectives to monitor bright-field, GFP, and pyoverdine fluorescence in Z-stack. ImageJ was used to process the images. Experiments were performed in triplicate, where at least 5 images were captured for each replicate, and representative images were shown. The scale bar in all images was 50 μm.

(G) Relative Quantification of Pyoverdine in Biofilms

Relative pyoverdine fluorescence levels in the biofilms were quantified from all biofilm images by ImageJ, using the equation: corrected total cell fluorescence (CTCF)=Integrated Density−(Area of selected cell×Mean fluorescence of background readings). Pyoverdine levels were positively correlated to biofilm cell numbers (CFU), and a standard curve plotting relative pyoverdine level against CFU was tabulated. Experiments were performed in triplicate, and results were shown as the mean±S.D.

(H) Quantification of Bacterial Counts by CFU

After harvesting the tails from euthanized animals after bacterial infection, the tissues were resuspended in 100 μl sterilized 0.9% (w/v) NaCl saline and ground manually by pellet pestle in 1.5-ml-microcentrifuge tubes (JET BIOFIL, China) until homogenization. The homogenized samples were diluted serially in 0.9% NaCl and then spread on centrimide agar (selective only for Pseudomonad growth) (Sigma-Aldrich, Germany). After incubation at 37° C. for 16 hrs, the colonies grown on the plates were enumerated. The CFU $ml^{-1}$ was tabulated by colony number×dilution factor×volume. Experiments were performed in triplicates, and the results are shown as mean±S.D.

(I) Quantification of c-Di-GMP Levels in Bacterial Biofilms by ELISA

Tail samples from healthy larvae fishes and the injured fishes were harvested after retrieval of sacrificed fish (48 h.p.i) from the device. The tail tissues were first ground on ice, followed by sonication at 30% amplitude for 10 mins with 20 s ON/20 s OFF output to lyse bacteria by ultrasonication machine (SFX 550, SSE-1, Branson, Emerson, USA). Per the manufacturer's protocol, c-di-GMP concentrations were tested by c-di-GMP ELISA kit (LMAI, Shanghai, China) and measured at $OD_{450\ mm}$ by the microplate reader (Tecan, Infinite M1000 Pro, Switzerland). The cytokines concentration was normalized by protein concentration, by which the protein concentration was measured by Nanodrop (Thermofisher, NanoDrop One, ND-One-W, USA) at $OD_{280\ mm}$. Experiments were performed in triplicate, and results were shown as the mean±S.D.

(J) Quantification of Inflammatory Cytokines by ELISA

Tail samples from healthy larvae fishes and the injured fishes were harvested after retrieval of sacrificed fish (48 h.p.i) from the device. The tail tissues were first ground on ice to disrupt tissues and release intracellular proteins, followed by sonication at 30% amplitude for 3 mins with 10 s ON/10 s OFF output by ultrasonication machine (SFX 550, SSE-1, Branson, Emerson, USA). Per the manufacturer's protocol, innate immunity cytokines (TNF-α, IL-2, and IL-6) in fishes were tested by ELISA kit (Bo Shen, Jiangsu, China) and measured at $OD_{450\ mm}$ by the microplate reader (Tecan, Infinite M1000 Pro, Switzerland). The cytokines concentration was normalized by protein concentration, by which the protein concentration was measured by Nanodrop (Thermofisher, NanoDrop One, ND-One-W. USA) at $OD_{280\ mm}$. Experiments were performed in triplicate, and the results are shown as the mean±S.D.

(K) Evaluation of SNP-Ciprofloxacin Combinatorial Therapy in In Vivo Wound Infection Model After establishing the wound infection model in the animals for 48 h.p.i. 1 μg $ml^{-1}$ ciprofloxacin (Sigma-Aldrich, Germany) and 10 μM Sodium nitroprusside (SNP; Sigma-Aldrich, Germany) were pumped into the device via 2 separate injection ports past the gradient mixer at the speed of 0.03 μl $min^{-1}$ for 24 hrs. After 24 hrs of treatment, the biofilms on the animals were evaluated by CFU $ml^{-1}$ and relative pyoverdine quantification. Experiments were performed in triplicate, and the results are shown as the mean±S.D.

Although the invention has been described in terms of certain embodiments, other embodiments apparent to those of ordinary skill in the art are also within the scope of this invention. Accordingly, the scope of the invention is intended to be defined only by the claims which follow.

INDUSTRIAL APPLICABILITY

The present invention is useful in the evaluation of vertebrate-microbe interactions under a set of well-defined conditions. The configuration of the microfluidic-based device for establishing the in vivo model and bioassay channels in the present invention facilitates scaling up to high throughput, routine basis screening system for pharmaceuticals and other chemical-manufacturing industries. The present invention also provides a platform for basic and clinical research to establish a wound infection model and conduct assays on vertebrate-microbe interactions with minimal training. Assembly and application of the microfluidic-based devices of the present invention is simple and fast. Multi-channel microfluidic design also allows high throughput assay and a high degree of multiplexing. Direct measurement or assessment of the samples in the microfluidic-based device by microscopy in the present invention, absent any prior cell sorting, isolation, and/or labelling steps as commonly used in conventional methods, also reflects the reality of the interactions between the vertebrate and microbes of interest, and increases the reliability of the assays.

REFERENCE

The following literatures are cited herein:

1. Yang. F., Gao, C., Wang. P., Zhang, G.-J. & Chen, Z. Fish-on-a-chip: microfluidics for zebrafish research. *Lab on a Chip* 16, 1106-1125, doi:10.1039/C6LC00044D (2016);
2. Saraceni, P. R., Romero, A., Figueras, A. & Novoa, B. Establishment of Infection Models in Zebrafish Larvae (*Danio rerio*) to Study the Pathogenesis of *Aeromonas hydrophila. Frontiers in Microbiology* 7, doi:10.3389/fmich.2016.01219 (2016);
3. Clatworthy, A. E. et al. <em>*Pseudomonas aeruginosa*</em> Infection of Zebrafish Involves both Host and Pathogen Determinants. 77, 1293-1303, doi:10.1128/IAI.01181-08% J Infection and Immunity (2009);
4. Rauta, P. R., Nayak, B. & Das, S. Immune system and immune responses in fish and their role in comparative immunity study: a model for higher organisms. *Immunol Lett* 148, 23-33, doi:10.1016/j.imlet.2012.08.003 (2012);
5. Khalili, A. & Rezai, P. Microfluidic devices for embryonic and larval zebrafish studies. *Brief Funct Genomics* 18, 419-432, doi:10.1093/bfgp/elz006 (2019);
6. Holloway, B. W. & Morgan, A. F. Genome Organization in *Pseudomonas. Annual Review of Microbiology* 40, 79-105, doi:10.1146/annurev.mi.40.100186.000455 (1986);
7. Rybtke, M. T. et al. Fluorescence-based reporter for gauging cyclic di-GMP levels in *Pseudomonas aeruginosa. Appl Environ Microbiol* 78, 5060-5069, doi:10.1128/AEM.00414-12 (2012);

8. Liu, S. Y., Leung. M. M.-L., Fang. J. K.-H. & Chua, S. L. Engineering a microbial 'trap and release' mechanism for microplastics removal. *Chemical Engineering Journal* 404, 127079. doi:https://doi.org/10.1016/j.cej.2020.127079 (2021);

9. Visca, P., Ciervo, A. & Orsi, N. Cloning and nucleotide sequence of the pvdA gene encoding the pyoverdin biosynthetic enzyme L-ornithine N5-oxygenase in *Pseudomonas aeruginosa. Journal of Bacteriology* 176, 1128, doi:10.1128/jb.176.4.1128-1140.1994 (1994);

10. Lambertsen, L., Sternberg, C. & Molin, S. Mini-Tn7 transposons for site-specific tagging of bacteria with fluorescent proteins. *Environmental Microbiology* 6, 726-732, doi:10.1111/j.1462-2920.2004.00605.x (2004);

11. Chua, S. L. et al. Bis-(3'-5')-cyclic dimeric GMP regulates antimicrobial peptide resistance in *Pseudomonas aeruginosa. Antimicrobial agents and chemotherapy* 57, 2066-2075, doi:10.1128/AAC.02499-12 (2013);

12. Chen, Y. et al. Multiple diguanylate cyclase-coordinated regulation of pyoverdine synthesis in *Pseudomonas aeruginosa. Environmental microbiology reports* 7. 498-507. doi:10.1111/1758-2229.12278 (2015);

13. Olucha, J., Meneely, K. M., Chilton, A. S. & Lamb, A. L. Two structures of an N-hydroxylating flavoprotein monooxygenase: ornithine hydroxylase from *Pseudomonas aeruginosa. J Biol Chem* 286, 31789-31798, doi:10.1074/jbc.M111.265876 (2011);

14. Kessler, B., de Lorenzo, V. & Timmis, K. N. A general system to integrate lacZ fusions into the chromosomes of gram-negative eubacteria: regulation of the Pm promoter of the TOL plasmid studied with all controlling elements in monocopy. *Molecular & general genetics: MGG* 233, 293-301, doi:10.1007/bf00587591 (1992);

15. Barnes, R. J., Leung, K. T., Schraft, H. & Ulanova, M. Chromosomal gfp labelling of *Pseudomonas aeruginosa* using a mini-Tn7 transposon: application for studies of bacteria-host interactions. *Canadian journal of microbiology* 54, 48-57, doi:10.1139/w07-118 (2008);

16. Chua. S. L. et al. Dispersed cells represent a distinct stage in the transition from bacterial biofilm to planktonic lifestyles. *Nature communications* 5, 4462. doi:10.1038/ncomms5462 (2014).

The invention claimed is:

1. A microfluidic-based device for establishing an in vivo model of wound infection on a host induced by pathogens, the device comprises a multi-layered structure, the multi-layered structure comprising:

a base layer;

an intermediate host-pathogen interface layer;

a bioassay layer; and a barrier layer, the base layer and barrier layer sandwiching the intermediate host-pathogen interface layer and the bioassay layer, respectively, for supporting the intermediate host-pathogen interface layer and the bioassay layer and preventing fluid from flowing through the intermediate host-pathogen interface layer and the bioassay layer in from leakage to the surroundings;

the bioassay layer comprising a plurality of fluid channels for generating a concentration gradient of one or more agents to be tested on the in vivo model and communicating with corresponding channels of the intermediate host-pathogen interface layer to form a continuous fluid flow system;

the intermediate host-pathogen interface layer comprising:

a plurality of channels, each configured to be periodically curved to form a sinusoidal waveform-like channel, and multiple compartments, each being disposed at the crest or trough of the sinusoidal waveform-like channel and separated from the sinusoidal waveform-like channel by an inner sidewall for forming an entrapment of fertilized embryo of the host, and each of the compartments has an extension with a decreasing cross-sectional area towards a direction opposite to a direction of the continuous fluid flow from the channels of the bioassay layer to the corresponding sinusoidal waveform-like channels of the intermediate host-pathogen interface layer for hatching the fertilized embryo of the host in the entrapment and subsequently inducing a wound on a tail portion of the host at a tip section of said extension.

2. The microfluidic-based device of claim 1, wherein the host is a vertebrate.

3. The microfluidic-based device of claim 2, wherein the vertebrate is selected from one or more types of fish.

4. The microfluidic-based device of claim 3, wherein the one or more types of fish comprise *Oryzias latipes* and *Danio rerio.*

5. The microfluidic-based device of claim 1, wherein the pathogens comprise bacteria, viruses, fungi, protozoa, and parasites.

6. The microfluidic-based device of claim 1, wherein the pathogens are bacteria comprising *P. aeruginosa* and bacterial species capable of forming biofilm-mediated wound infection on the host.

7. The microfluidic-based device of claim 1, wherein the intermediate host-pathogen interface layer and the bioassay layer are arranged laterally at substantially the same horizontal level.

8. The microfluidic-based device of claim 1, wherein the intermediate host-pathogen interface layer is sandwiched between the base and bioassay layers.

9. The microfluidic-based device of claim 1, wherein the multi-layered structure is made of a material which is flexible, bendable, biocompatible, and inert to biological and chemical reactions with any of the host animals, pathogens, and agents to be applied to the bioassay layer.

10. The microfluidic-based device of claim 1, wherein the material for making the multi-layered structure is selected from polydimethylsiloxane.

11. The microfluidic-based device of claim 1, wherein the inner sidewall is water permeable only to allow fluid and substances to penetrate from the sinusoidal waveform-like channel of the intermediate host-pathogen interface layer to the corresponding compartment while the fertilized embryo or host animal remains entrapped when fluid flows through the sinusoidal waveform-like channel.

12. The microfluidic-based device of claim 1, wherein the bioassay layer further comprises a plurality of fluid inlets for introducing fluid and agents to be tested with a concentration gradient into the intermediate host-pathogen interface layer through the continuous fluid flow system.

13. The microfluidic-based device of claim 12, wherein the agents to be tested comprises one or more chemical or biological agents.

14. The microfluidic-based device of claim 1, wherein each compartment has at least 1-mm depth.

15. The microfluidic-based device of claim 1, further comprises a layer for introducing fluid containing a different agent of interest from those introduced into the bioassay layer and said layer comprises multiple channels for generating a concentration gradient before the fluid containing the different agent of interest flows into the intermediate host-pathogen interface layer.

16. A method for screening potential drug candidates for treating inflammatory diseases in a subject caused by pathogens, comprising:

providing a pathogenic infection in an in vivo model established on the microfluidic-based device of claim 1;

applying a fluid containing the potential drug candidate to the in vivo model through one or more fluid channels of the microfluidic-based device;

assessing therapeutic effects of the potential drug candidate on the inflammatory diseases of the in vivo model qualitatively and quantitatively; and comparing the qualitative and quantitative assessment results of the therapeutic effects of the potential drug candidate with those of a known therapeutic agent for treating the same inflammatory diseases on the same subject to determine whether the potential drug candidate is a potential anti-inflammatory agent.

17. The method of claim 16, wherein said providing the in vivo model in the microfluidic-based device comprises:

entrapping fertilized embryos of a host animal into each of the compartments of multiple channels of the intermediate host-pathogen interface layer by providing a water-permeable inner sidewall arranged between each of the compartments and an adjacent channel thereto such that only fluid and substances penetrable to the water-permeable inner sidewall can pass through the water-permeable inner sidewall while the fertilized embryos of the host animal are entrapped in the compartment;

hatching the fertilized embryos until the host animal reaches larval stage;

inducing a wound on the skin of a tail portion of the host animal through a tip section of the extension of the compartment; and introducing pathogens to the compartment to co-culture with the host animal in the same compartment to establish a wound infection on the skin of the tail portion of the host animal;

monitoring the wound infection qualitatively and quantitatively to verify the establishment and assess the extent of wound infection.

18. The method of claim 17, wherein the host animal is selected from a fish.

19. The method of claim 18, wherein the fish comprises *Oryzias latipes* and *Danio rerio*.

20. The method of claim 17, wherein the pathogens comprise bacteria, viruses, fungi, protozoa, and parasites, or any combination thereof.

21. The method of claim 20, wherein the pathogens comprise planktonic cells and multicellular aggregates encased in a biofilm matrix formed on or adjacent to the wound induced on the skin of the tail portion of the host animal.

22. The method of claim 17, wherein the assessment of the extent of the wound infection established on the host animal comprises performing bioassays of a plurality of cytokines involved in said wound infection, observing morphological, cellular composition, and genetic changes in the biofilm formed on the infected wound by the pathogens or at the infection region of the host animal, and quantifying the expression of biomarkers, genetic markers, and presence of metabolites relating to the biofilm formation or wound infection.

23. The method of claim 16, wherein said applying the fluid containing the potential drug candidate to the in vivo model comprises establishing a concentration gradient from a first fluid channel to the last fluid channel of the bioassay layer of the microfluidic-based device.

24. The method of claim 16, wherein said assessing the therapeutic effects of the potential drug candidate on the inflammatory diseases of the in vivo model qualitatively and quantitatively, includes:

observing the morphological change of the biofilm formed by the pathogens under microscopy and/or through histology; and quantifying the expression of biomarkers specific to the biofilm formation on the infected wound of the host animal.

25. The method of claim 17, wherein the pathogens are selected from *P. aeruginosa*.

26. The method of claim 25, wherein a biofilm formed by *P. aeruginosa* expresses a specific biomarker that scavenges iron from the host animal or the surrounding fluid in the compartment.

27. The method of claim 26, wherein the specific biomarker of the biofilm formed by *P. aeruginosa* is pyoverdine.

28. The method of claim 27, wherein the pyoverdine expression is directly detectable under fluorescent microscopy absent labeling agent.

29. The method of claim 16, wherein said comparing the qualitative and quantitative assessment results of the therapeutic effects of the potential drug candidate with those of a known therapeutic agent for treating the same inflammatory diseases on the same model, comprises:

comparing the qualitative and quantitative assessment results of the therapeutic effects of the potential drug candidate with those of the known therapeutic agent eradicating the pathogenic infection due to biofilm formation by the same species of pathogens on the same in vivo model, wherein the qualitative and quantitative assessment results include histological analyses and quantification of the local or systemic expression of specific biomarkers, genetic markers, and presence of metabolites relating to the biofilm formation or infection in said in vivo model.

30. The method of claim 16, wherein the subject comprises non-human mammals and humans.

* * * * *